(12) United States Patent
Wisniewski et al.

(10) Patent No.: US 8,906,382 B2
(45) Date of Patent: Dec. 9, 2014

(54) METHOD FOR TREATING AMYLOID DISEASE

(75) Inventors: Thomas Wisniewski, Staten Island, NY (US); Fernando R. Goni, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/553,566

(22) Filed: Jul. 19, 2012

(65) Prior Publication Data

US 2013/0022630 A1 Jan. 24, 2013

Related U.S. Application Data

(60) Provisional application No. 61/509,442, filed on Jul. 19, 2011.

(51) Int. Cl.
*A61K 39/00* (2006.01)
*C07K 1/00* (2006.01)
*C07K 14/47* (2006.01)

(52) U.S. Cl.
CPC .......... *A61K 39/0005* (2013.01); *C07K 14/4711* (2013.01)
USPC ........................................ 424/185.1; 530/323

(58) Field of Classification Search
CPC ............... C07K 16/18; C07K 14/4711; G01N 33/6896; G01N 2800/2821; G01N 2333/4709; G01N 2500/00; G01N 2800/28; A61K 2039/505; A61K 38/00; A61K 2300/00; A61K 39/0007; A61K 38/1709; A61K 39/3955
See application file for complete search history.

(56) References Cited

U.S. PATENT DOCUMENTS

| | | | |
|---|---|---|---|
| 4,180,562 A | 12/1979 | Patterson et al. | |
| 5,080,896 A | 1/1992 | Visser et al. | |
| 5,434,170 A | 7/1995 | Andrulis, Jr. | |
| 5,688,651 A | 11/1997 | Solomon | |
| 5,695,766 A | 12/1997 | Paul et al. | |
| 5,843,446 A | 12/1998 | Ladd et al. | |
| 5,948,763 A | 9/1999 | Soto-Jara et al. | |
| 6,022,859 A | 2/2000 | Kiessling et al. | |
| 6,274,615 B1 | 8/2001 | Pappolla et al. | |
| 6,462,171 B1 | 10/2002 | Soto et al. | |
| 6,670,195 B1 | 12/2003 | Ghiso et al. | |
| 6,713,450 B2 | 3/2004 | Frangione et al. | |
| 6,866,849 B2 | 3/2005 | Schenk | |
| 6,962,707 B2 | 11/2005 | Schenk | |
| 7,427,655 B2 | 9/2008 | Frangione et al. | |
| 7,479,482 B2 | 1/2009 | Frangione et al. | |
| 7,632,816 B2 | 12/2009 | Wisniewski et al. | |
| 7,700,107 B2 | 4/2010 | Frangione et al. | |
| 7,902,328 B2* | 3/2011 | Hillen et al. ................. | 530/324 |
| 2002/0009445 A1 | 1/2002 | Du et al. | |
| 2002/0037290 A1 | 3/2002 | Armen | |
| 2002/0077288 A1 | 6/2002 | Frangione et al. | |
| 2003/0166558 A1 | 9/2003 | Frangione et al. | |
| 2004/0043935 A1 | 3/2004 | Frangione et al. | |
| 2004/0214774 A1 | 10/2004 | Wisniewski et al. | |
| 2005/0019330 A1 | 1/2005 | Schenk | |
| 2006/0199771 A1 | 9/2006 | Chalifour et al. | |
| 2007/0010435 A1 | 1/2007 | Frangione et al. | |
| 2007/0122421 A1 | 5/2007 | Medzhitov | |
| 2008/0050383 A1 | 2/2008 | Sigurdsson et al. | |
| 2009/0081204 A1 | 3/2009 | Frangione et al. | |
| 2009/0163420 A1 | 6/2009 | Frangione et al. | |
| 2009/0175853 A1 | 7/2009 | Frangione et al. | |
| 2010/0284909 A1 | 11/2010 | Wisniewski et al. | |
| 2010/0298202 A1 | 11/2010 | Jansen-West et al. | |
| 2011/0117100 A1* | 5/2011 | Britschgi et al. ........... | 424/139.1 |
| 2013/0022544 A1 | 1/2013 | Wisniewski et al. | |
| 2013/0045216 A1 | 2/2013 | Frangione et al. | |

FOREIGN PATENT DOCUMENTS

| | | |
|---|---|---|
| EP | 0908727 A1 | 4/1999 |
| WO | WO 93/23432 A1 | 11/1993 |
| WO | WO 94/17197 A1 | 8/1994 |
| WO | WO 95/31996 A1 | 11/1995 |
| WO | WO 96/39834 A1 | 12/1996 |
| WO | WO 98/15179 A1 | 4/1998 |
| WO | WO 98/39653 A1 | 9/1998 |
| WO | WO 99/27944 A1 | 6/1999 |
| WO | WO 99/27949 A1 | 6/1999 |
| WO | WO 99/48489 A2 | 9/1999 |
| WO | WO 00/71671 A2 | 11/2000 |
| WO | WO 00/72800 A2 | 12/2000 |
| WO | WO 00/72880 A2 | 12/2000 |
| WO | WO0190182 A2 | 11/2001 |
| WO | WO 02/11669 A2 | 2/2002 |
| WO | WO 03/044051 A1 | 5/2003 |
| WO | WO 03/051374 A2 | 6/2003 |
| WO | WO03045128 A2 | 6/2003 |
| WO | WO2004056318 A8 | 6/2006 |
| WO | WO2009009396 A2 | 1/2009 |
| WO | WO2004087733 A3 | 3/2009 |
| WO | WO 2010/016912 A2 | 2/2010 |
| WO | WO2010129674 A3 | 2/2011 |

OTHER PUBLICATIONS

Jackson DC et al. (1997) Free radical induced polymerization of synthetic peptides into polymeric immunogens. Vaccine, 15(15):1697-1705.*

Levine H. (1995) Soluble multimeric Alzheimer beta(1-40) pre-amyloid complexes in dilute solution. Neurobiol. Aging, 16(5):755-764.*

Wisniewski T et al. (2009) Immunotherapy targeting abnormal protein conformation. Alzheimer's & Dementia, 5(4) Suppl. 1:P113, Abstract #O2-05-03.*

International Search Report and Written Opinion of the International Searching Authority for International Application No. PCT/US12/47424, mailed Oct. 4, 2012.

(Continued)

*Primary Examiner* — Kimberly A Ballard
(74) *Attorney, Agent, or Firm* — Troutman Sanders LLP

(57) ABSTRACT

The invention relates to methods for treating human amyloid disease by administration of modified Aβ peptide immunogens.

4 Claims, 7 Drawing Sheets

(56) References Cited

OTHER PUBLICATIONS

Asuni et al., "Vaccination of Alzheimer's model mice with Abeta derivative in alum adjuvant reduces Abeta burden without microhemorrhages," Eur J Neurosci. (2006) vol. 24, No. 9, pp. 2530-2542.
Boutajangout et al., "Diminished amyloid-beta burden in Tg2576 mice following a prophylactic oral immunization with a salmonella-based amyloid-beta derivative vaccine," J Alzheimers Dis. (2009) vol. 18, No. 4, pp. 961-972.
Frenkel et al., "High affinity binding of monoclonal antibodies to the sequential epitope EFRH of beta-amyloid peptide is essential for modulation of fibrillar aggregation," J Neuroimmunol (1999) vol. 95, pp. 136-142.
Goni et al., "Immunomodulation targeting abnormal protein conformation reduces pathology in a mouse model of Alzheimer's disease," PLoS One. (2010) vol. 5, issue 10, pp. e13391.
Klyubin et al., "Amyloid beta protein dimer-containing human CSF disrupts synaptic plasticity: prevention by systemic passive immunization," J Neurosci. (2008) vol. 28, No. 16, pp. 4231-4237.
Sadowski et al., "Targeting prion amyloid deposits in vivo," J Neuropathol Exp Neurol. (2004) vol. 63, No. 7, pp. 775-784.
Sadowski et al., "A synthetic peptide blocking the apolipoprotein E/beta-amyloid binding mitigates beta-amyloid toxicity and fibril formation in vitro and reduces beta-amyloid plaques in transgenic mice," Am J Pathol. (2004) vol. 165, No. 3, pp. 937-948.
Sadowski et al., "Blocking the apolipoprotein E/amyloid-beta interaction as a potential therapeutic approach for Alzheimer's disease," Proc Natl Acad Sci U S A. (2006) vol. 103, No. 49, pp. 18787-18792. Epub Nov. 20, 2006.
Sadowski et al., "Disease modifying approaches for Alzheimer's pathology," Curr Pharm Des. (2007) vol. 13 No. 19, pp. 1943-1954.
Sigurdsson et al., "An attenuated immune response is sufficient to enhance cognition in an Alzheimer's disease mouse model immunized with amyloid-beta derivatives," J Neurosci. (2004) vol. 24, No. 28, pp. 6277-6282.
Trouche et al., "Antibody response and plasma Abeta1-40 levels in young Microcebus murinus primates immunized with Abeta1-42 and its derivatives" Vaccine. (2009) vol. 27, No. 7, pp. 957-964. Epub Dec. 27, 2008.
Wisniewski et al., "Immunological and anti-chaperone therapeutic approaches for Alzheimer disease," Brain Pathol. (2005) vol. 15, No. 1, pp. 72-77.
Wisniewski et al., "Therapeutic approaches for prion and Alzheimer's diseases," FEBS J. (2007) vol. 274, No. 15, pp. 3784-3798. Epub Jul. 6, 2007.
Wisniewski et al., "Amyloid-beta immunisation for Alzheimer's disease," Lancet Neurol. (2008) vol. 7, No. 9, pp. 805-811. Epub Jul. 28, 2008.
Wisniewski et al., "Preventing beta-amyloid fibrillization and deposition: beta-sheet breakers and pathological chaperone inhibitors," BMC Neurosci. (2008) vol. 3, No. 9, Suppl 2:S5.
Wisniewski, "AD vaccines: conclusions and future directions," CNS Neurol Disord Drug Targets (2009) vol. 8, No. 2, pp. 160-166.
Wisniewski et al., "Immunotherapeutic approaches for Alzheimer's disease in transgenic mouse models," Brain Struct Funct. (2010) vol. 214, Nos. 2-3, pp. 201-218. Epub Dec. 10, 2009.
Wisniewski et al., "Vaccination as a therapeutic approach to Alzheimer's disease," Mt Sinai J Med. (2010) vol. 77, No. 1, pp. 17-31.
Wisniewski et al., "Murine models of Alzheimer's disease and their use in developing immunotherapies," Biochim Biophys Acta. (2010) vol. 1802, No. 10, pp. 847-859. Epub May 13, 2010.
Wisniewski et al., "Immunomodulation for prion and prion-related diseases," Expert Rev Vaccines. (2010) vol. 9, No. 12, pp. 1441-1452.
Yang et al., "Blocking the apolipoprotein E/amyloid-β interaction reduces fibrillar vascular amyloid deposition and cerebral microhemorrhages in TgSwDI mice," J Alzheimers Dis. (2011) vol. 24, No. 2, pp. 269-285.

Bendig 1995 "Humanization of rodent monoclonal antibodies by CDR grafting" Methods: a companion to methods in enzymology 8:83-93.
Habicht et al 2007 "Directed selection of a conformational antibody domain that prevents mature amyloid fibril formation by stabilizing a(beta) protofibrils" PNAS 1 04(49): 19232-19237.
Holt et al. 2003 "Domain antibodies: proteins for therapy" Trends in biotech 21 (11): 484-490.
Kayed et al 2007 "Fibril specific, conformation dependent antibodies recognize a generic epitope common to amyloid fibrils and fibrillar oligomers that is absent in prefibrillar oligomers" Molec Neurodegen 2(18):1-11.
O'Nualiain and Wetzel "Conformational Abs recognizing a generic amyloid fibril epitope" PNAS 99(3):1485-1490, 2002.
Carro et al., "Serum insulin-like growth factor I regulates brain amyloid-beta levels", Nat Med, vol. 8, pp. 1390-1397, 2002.
Gasset, M. et aL "Perturbation of the secondary structure of the scrapie prion protein under conditions that alter infectivity;" Proc. NatL Acad. Sci. USA vol. 90, pp. 1-5. (1993).
Zlokovic et al. Brain uptake of circulating apolipoproteins J and E complexed to Alzheimer's amyloid beta, Biochem Biophys Res Commun, vol. 205, pp. 1431-1437, 1994.
Zlokovic et al., Glycoprotein 330/megalin: probable role in receptor-mediated transport of apolipoprotein J alone and in a complex with Alzheimer's disease amyloid? at the blood-brain and blood-cerebrospinal fluid barriers, Proc Natl Acad Sci USA, vol. 93, pp. 4229-4234, 1996.
Van Regenmortel et al. "D-peptides as Immunogens and Diagnostic Reagents," 1998. Current Opinion in Biotechnology 9:377-382.
Benkirane 1993. "Antigenicity and immunogenicity of modified synthetic peptides containing D-amino acid residues. Antibodies to a D-enantiomer do recognize the parent L-hexapeptide and reciprocally". Journal of Biological Chemistry 268:26279-26285.
Bodles 2001. "Identification of the region of non-Ab component of Alzheimer's disease amyloid responsible for its aggregation and toxicity." Journal of Neurochemistry 78:384-395.
Conway 2000. "Fibrils Formed in Vitro from a-Synuclein and Two Mutant Forms Linked to Parkinson's Disease are Typical Amyloid"Biochemistry 39:2552-2563.
Lowenadler 1990. "Enhanced immunogenicity of recombinant peptide fusions containing multiple copies of a heterologous T helper epitope." European Journal of Immunology 20:1541-1545.
Aguado et al., "Meeting Report-Novel adjuvants currently in clinical testing Nov. 2-4, 1998, Foundation Mérieux, Annecy, France: A meeting sponsored by the World Health Organization." Vaccine (1999) 17:2321-2328.
Biere et al., "Parkinson's disease-associated alpha-synuclein is more fibrillogenic than beta- and gamma-synuclein and cannot cross-seed its homologs."J. Biol Chem (2000) 275:34574-34579.
Bueler et al,. "Mice Devoid of PrP are Resistant to Scrapie," Cell (1993) 73:1339-1347.
Bueler et al., "Normal development and behavior of mice lacking the neuronal cell-surface PrP protein", Nature (1992) 356:577-582.
Buschle et al., "Transloading of tumor antigen-derived peptides into antigen-presenting cells," Proc. Natl. Sci. USA (1997) 94:3256-3261.
Calero et al., "Distinct properties of wild-type and the amyloidogenic human cystatin C variant of hereditary cerebral hemorrhage with amyloidosis, Icelandic type." J of Neurochemistry (2001) 77:628-637.
Chesebro et al., "Identification of scrapie prion protein-specific mRNA in scrapie-infected and uninfected brain." Nature (1985) 315:331-333.
Deierkauf et al., "Phygocytosis by rabbit polymorphonuclear leukocytes: the effect of albumin and polyamine acids on latex uptake" J. Cell Physiol. (1977) 92:169-175.
Di Nicola et al., "Large-scale feasibility of gene transduction into human cd34+cell-derived dendritic cells by adenoviral/polycation complex", Brit. J. of Haematology (2000) 111:344-350.
Farmer et al., 1993. "Human immune response to cationized proteins. II. Characterization of interaction of cationized diphtheria toxoid with human mononuclear cells." Cellular Immunology 146(1):198-209.

(56) References Cited

OTHER PUBLICATIONS

Findeis et al., "Approaches to discovery andcharacterization of inhibitors of amyfoid b-peptide polymerization," Biochim Biophys Acta (2000) 1502:76-84.
Frenkel et al., "Modulation of Alzheimer's b-Amyloid Neurotoxicity by Site-Directed Single-Chain Antibody". Neuroimmunomodulation (1999) 6:444 (P43).
Futaki et al., "Arginine-rich peptides: an abundant source of membrane-permeable peptides having potential as carriers for intracellular protein delivery", J. of Biological Chem. (2001) 276:5836-5840.
Ghetti et al., "Familial Gerstmann-Sträussler-Scheinker disease with neurofibrillary tangles." Mol Neurobiol (1994) 8:41-48.
Ghetti et al., "Vascular variant of prion protein cerebral amyloidosis with tau-positive neurofibrillary tangles: the phenotype of the stop codon 145 mutation in PRNP" Proc Natl Acad Sci USA (1996) 93:744-748.
Giasson et al., "Neuronal alpha-synucleinopathy with severe movement disorder in mice expressing A53T human alpha-synuclein" Neuron (2002) 34:521-533.
Goedert et al., "a-Synuclein and neurodegenerative diseases." Nat Rev Neurosci (2001) 2:492-501.
Horwich et al., "Deadly Conformations—Protein Misfolding in Prion Disease", Cell (1997) 89:499-510.
Hsiao et al., "Serial transmission in rodents of neurodegeneration from transgenic mice expressing mutant prion protein", Proc Natl Acad Sci USA (1994) 91:9126-9130.
Johnson et al., "Islet amyloid, islet amyloid polypeptide, and diabetes mellitus.", N Engl J Med (1989) 321:513-518.
Kaytor et al., "Aberrant Protein Deposition and Neurological Disease" J Biol Chem (1999) 274:37507-37510.
Kisilevsky et al., "Anti-amyloid drugs: Potential in the treatment of diseases associated with aging", Drugs & Aging (1996) 8:75-83.
Kretzschmar et al., "Scrapie prion proteins are synthesized in neurons", Am J Pathol (1986) 122:1-5.
Martinez-Fong et al., "Nonenzymatic glycosylation of poly-L-lysine: a new tool for targeted gene delivery", Hepatology, (1994) 20:1602-1608.
Moriarty et al., "Effects of Sequential Proline Substitutions on Amyloid Formation by Human Amylin" Biochemistry (1999) 38:1811-1818.
Oesch et al., "A cellular gene encodes scrapie PrP 27-30 protein." Cell (1985) 40:735-746.
Pallitto et al., "Recognition Sequence Design for Peptidyl Modulators of ?-Amyloid Aggregation and Toxicity" Biochemistry (1999) 38:3570-3578.
Peterson et al., "Polyamino Acid Enhancement of Bacterial Phagocytosis by Human Polymorphonuclear Leukocytes, and Peritoneal Macrophages",Infection and Immunity (1984) 43:561-566.
Prusiner et al., "Prion Protein Biology", Cell (1998) 93:337-348.
Prusiner et al., "Perturbation of the secondary structure of the scrapie prion protein under conditions that alter infectivity", Proc Natl Acad Sci USA (1993) 90:10608-10612.
Rubinsztein et al., "Intracellular inclusions, pathological markers in diseases caused by expanded polyglutamine tracts?", J Med Genet (1999) 36:265-270.
Schenk et al., Immunization with amyloid-beta attenuates Alzheimer-disease-like pathology in the PDAPP mouse. Nature (1999) 400:173-177.
Schwarzenberger et al., "Poly-L-lysine-based molecular conjugate vectors: a high efficiency gene transfer system for human progenitor and leukemia cells.", Amer. J. of the Medical Sciences (2001) 321:129-136.
Serpell et al., "Fiber diffraction of synthetic a-synuclein filaments shows amyloid-like cross-b conformation", Proc Natl Acad Sci USA (2000) 97:4897-4902.
Shen et al., "Disulfide spacer between methotrexate and poly(D-lysine). A probe for exploring the reductive process in endocytosis", J. of Biol. Chem. (1985) 260:10905-10908.

Sigurdsson et al., "Immunization with a nontoxic/nonfibrillar amyloid-b homologous peptide reduces Alzheimer's Disease-associated pathology in transgenic mice."Amer. Journal of Pathology (2001) 159:439-447.
Sigurdsson et al., "Immunization delays the onset of prion disease in mice.", Amer. Journal of Pathology (2002) 161:13-17.
Sigurdsson et al., "Immunization for Alzheimer's Disease. Drug Development Research", Drug Development Research (2002) 56:135-142.
Sigurdsson et al., "In Vivo Reversal of Amyloid-b Lesions in Rat Brain". J. of Neuropathology and Exp. Neurology (2000) 59:11-17.
Sigurdsson et al., "Infectivity of amyloid diseases", Trends in Mol. Medicine (2002) 8:411-413.
Solomon et al., "Disaggregation of Alzheimer beta-amyloid by site-directed mAb",Proc. Natl. Acad. Sci. USA (1997) 94:4109-4112.
Soto et al., "Reversion of prion protein conformational changes by synthetic beta-sheet breaker peptides." Lancet (2000) 355:192-197.
Soto et al., "b-sheet breaker peptides inhibit fibrillogenesis in a rat brain model of amyloidosis: Implications for Alzheimer's therapy,"Nat Med (1998) 4:822-826.
Spillantini et al., "Alpha-synuclein in Lewy bodies", Nature (1997) 388:839-840.
Tagliavini et al., "Synthetic peptides homologous to prion protein residues 106-147 form amyloid-like fibrils in vitro", Proc. Natl. Acad. Sci. USA (1993) 90:9678-9682.
Telling et al., "Interactions between wild-type and mutant prion proteins modulate neurodegeneration in transgenic mice." Genes & Dev (1996) 10:1736-1750.
Wang et al., 1989. "Endocytosis of Horseradish Peroxidase-Poly-Lysine Conjugate by Glomerular Epithelial Cells: An *in vivo* Study". J Pathol 159: 159-167.
Westermark et al., "Islet Amyloid Polypeptide: Pinpointing Amino Acid Residues Linked to Amyloid Fibril Formation", Proc Natl Acad Sci USA (1990) 87:5036-5040.
Wisniewski and Sigurdsson, 2002. "Immunization treatment approaches in Alzheimer's and prion diseases". Curr Neurol and Neurosci Rpts 2(2):400-404.
Wisniewski et al., 2002. "Therapeutics in Alzheimer's and Prion Diseases". Biochemical Society Transactions 30: 574-578.
Wood et al., "Prolines and amyloidogenicity in fragments of the Alzheimer's peptide beta/A4", Biochemistry (1995) 34:724-730.
Poduslo et al., "beta-sheet Breaker Peptide Inhibitor of Alzheimer's Amyloidogenesis with Increased Blood-Brain Barrier Permeability and Resistance to Proteolytic Degradation in Plasma", J. Neurobiol., 1999, 371-382.
Goni F et al. (2008) High titers of mucosal and systemic anti-PrP antibodies abrogate oral prion infection in mucosal-vaccinated mice. Neurosci. 153:679-686.
Lauren J et al. (Feb. 2009) Cellular prion protein mediates impairment of synaptic plasticity by amyloid-beta oligomers. Nature, 457:1128-1132.
International Search Report and Written Opinion for PCT/US2012/046941 (Jan. 30, 2013).
Sadler et al., "Synthetic Peptide Epitope-Based Polymers: Controlling Size and Determining the Efficiency of Epitope Incorporation," J. Pept. Res. 60(3):150-158 (2002).
Stratagene Catalog, p. 215 (1991).
Alberts et al., Molecular Biology of the Cell, pp. 129-130 (1994).
Ghanta. et ai, 1996. "A strategy for designing inhibitors of betaamyloid toxicity". 1. Biol. Chem. 271(47): 29525-29528.
Maillere, et al., 1995. "Fine chemical modifications at N- and C-termini enhance peptide presentation to T cells, by increasing the lifespan of both free and MHC-complexed peptides". Molecular Immunology 32(17/18): 1377-1385.
Yankner, et al., 1990. "Neurotrophic and neurotoxic effects of amyloid beta protein: reversal by tachy kinin neuropeptides". Science 250(4978): 279-282.
Pike, et al., 1993. "Neurodegeneration induced by beta-amyloid peptides in vitro: the role of peptide assembly state". J. Neuroscience 13(4) 1676-1687.
Zhou et al., "cDNA sequence of the 3'-coding region of PVY genome (the Chinese isolate)," Nucleic Acids Res., 18:5554, 1990.

(56) References Cited

OTHER PUBLICATIONS

Yamada et al., "Complementary DNA for the mouse homolog of the human amyloid beta protein precursor," Biochem. Biophys. Res. Commun., 149:665-671,1987.

Castillo G.M. Perlecan binds to the beta-amyloid proteins (A beta) of Alzheimer's disease, accelerates A beta fibril formation, and maintains A beta fibril stability, J Neurochem., vol. 69(6), pp. 2452-2465, 1997.

Demattos et al., Clusterin promotes amyloid plaque formation and is critical for neuritic toxicity in a mouse model of Alzheimer's disease, Proc Natl Acad Sci USA, vol. 99, pp. 10843-10848, 2002.

Findeis Ma et al., Approaches to discovery and characterization of inhibitors of amyfoid beta-peptide polymerization, Biochim Biophys Acta, vol. 1502, pp. 76-84, 2000.

Ghersi-Egea et al., Fate of cerebrospinal fluid-borne amyloid beta-peptide: rapid clearance into blood and appreciable accumulation by cerebral arteries, J Neurochem, vol. 67(2), pp. 880-883, 1996.

Ghiso et al., The cerebrospinal-fluid soluble form of Alzheimer's amyloid beta is complexed to SP-40,40 (apolipoprotein J),an inhibitor of the complement membrane-attack complex, Biochem J, vol. 293, pp. 27-30, 1993.

Ghiso et al., Unifying features of systemic and cerebral amyloidosis, Mol Neurobiol.,vol. 8, pp. 49-64, 1994.

Ghiso et al. Alzheimer's soluble amyloid β is a normal component of human urine, FEBS Letters, vol. 408, pp. 105-108, 1997.

International Search Report for PCT/US03/40744, dated Jan. 26, 2006.

Jarrett et al. The carboxy terminus of the beta amyloid protein is critical for the seeding of amyloid formation: implications for the pathogenesis Alzheimer's disease, Biochemistry, vol. 32, pp. 4693-4697, 1993.

Jarrett et al., Seeding one-dimensional crystallization of amyloid: a pathogenic mechanism in Alzheimer's disease and scrapie? Cell, vol. 73, pp. 1055-1058, 1993.

Ji et al., Amyloid beta 40/42 clearance across the blood-brain barrier following intraventricular injections in wild-type, apoE knock-out and human apoE3 or E4 expressing transgenic mice, . Journal of Alzheimer's Disease, vol. 3, pp. 23-30, 2001.

Jordan J., Isoform-Specific Effect of Apolipoprotein E on Cell Survival and beta-Amyloid-Induced Toxicity in Rat Hippocampal Pyramidal Neuronal Cultures, J. Neurosci., vol. 18, No. 1, pp. 195-204, 1998.

Koudinov et al., The soluble form of Alzheimer's amyloid beta protein is complexed to high density lipoprotein 3 and very high density lipoprotein in normal human plasma, Biophys Res Commun, vol. 205, No. 2, pp. 1164-1171, 1994.

Matsubara, et al. Characterization of Apolipoprotein J-Alzheimer's Aβ Interaction. The Journal of Biological Chemistry, vol. 270, No. 13, pp. 7563-7567, 1995.

Matsuoka, Y. Novel Therapeutic Approach for the Treatment of Alzheimer's Disease by Peripheral Administration of Agents with an Affinity to beta-Amyloid, J. Neurosci, vol. 23, No. 1. pp. 29-33, 2003.

Pepys et al., Targeted Pharmacological Depletion of Serum Amyloid P Component for Treatment of Human Amyloidosis, Nature, vol. 417, pp. 254-259, 2002.

Permanne et al, Detection of apolipoprotein E/Dimeric Soluble Amyloid J3 Complexes in Alzheimer's Disease Brain Supernatants, Biochemical and Biophysical Research Communications, vol. 240, pp. 715-720, 1997.

Seubert et al., Isolation and quantification of soluble Alzheimer's beta-peptide from biological fluids, Nature, vol. 359, pp. 325-327, 1992.

Shibata et al., Clearance of Alzheimer's amyloid-ss(1-40) peptide from brain by LDL receptor related protein-1 at the blood-brain barrier, J Clin Invest, vol. 106, pp. 1489-1499, 2000.

Shoji et al., Production of the Alzheimer amyloid beta protein by normal proteolylic processing, Science, vol. 258, pp. 126-129, 1992.

Soto et al., Beta-Sheet breaker peptides inhibit fibrillogenesis in a rat brain model of amyloidosis: implications for Alzheimer's therapy, Nat Med, vol. 4, pp. 822-826, 1998.

Vickers et al., A vaccine against Alzheimer's disease: developments to date, Drugs Aging, vol. 197(7), pp. 487-494, 2002.

Ylera et al., Selection of RNA Aptamer to the Alzheimer's disease amyloid peptide, Biochem. Biophys. Res. Comm. , vol. 290, pp. 1583-1588, 2002.

Wisniewski et al., Short Communication: Acceleration of Alzheimer's Fibril Formation by Apolipaprotein E In Vitro, American Journal of Pathology, vol. 145, No. 5, pp. 1030-1035, 1994.

Barghorn et al. "Globular amyloid β-peptide$_{1-42}$ oligomer—a homogenous and stable neuropathological protein in Alzheimer's disease" (2005) Journal of Neurochemistry 95:834-847.

Friedman et al. "Surfactant Effects on Amyloid Aggregation Kinetics" (2011) Journal of Molecular Biology 414:303-312.

Gellermann et al. "Aβ-globulomers are formed independently of the fibril pathway" (2008) Neurobiology of Disease 30:212-220.

Hayden et al. "Amyloid β-protein oligomers and Alzheimer's disease" (2013) Alzheimer's Research & Therapy 5:60.

Helenius et al. "Solubilization of Membranes by Detergents" (1975) Biochimica et Biophysica Acta 415:29-79.

Hillen et al. "Generation and Therapeutic Efficacy of Highly Oligomer-Specific β-Amyloid Antibodies" (2010) The Journal of Neuroscience 30(31):10369-10379.

Migneault et al. "Glutaraldehyde: behavior in aqueous solution, reaction with proteins, and application to enzyme crosslinking" (2004) BioTechniques 37:790-802.

Montserret et al. "Involvement of Electrostatic Interactions in the Mechanism of Peptide Folding Induced by Sodium Dodecyl Sulfate Binding" (2000) Biochemistry, 39(29):8362-8373.

Nielsen et al. "Unfolding of β-Sheet Proteins in SDS", (2007) Biophysical Journal 92:3674-3685.

Simons et al. "Formation of protein micelles from amphiphilic membrane proteins" (1978) Proc. Natl. Acad. Sci. 75(11):5306-5310.

Tew et al. "Stabilization of Neurotoxic Soluble β-Sheet-Rich Conformations of the Alzheimer's Disease Amyloid-β Peptide" (2008) Biophysical Journal 94:2752-2766.

Wahlström et al. "Secondary structure conversions of Alzheimer's Aβ(1-40) peptide induced by membrane-mimicking detergents" (2008) FEBS Journal 275:5117-5128.

Wisniewski et al. "Immunotherapy for Alzheimer's Disease" (2014) Biochemical Pharmacology 88:499-507.

Yu et al. "Structural Characterization of a Soluble Amyloid β-Peptide Oligomer" (2009) Biochemistry 48:1870-1877.

* cited by examiner

Immunohistological Analysis

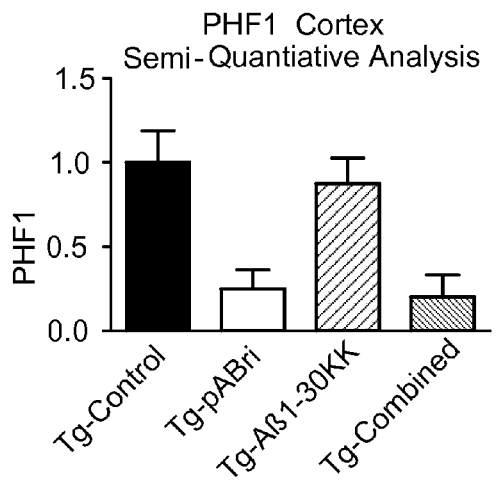

p=0.0003 one way ANOVA
post-hoc: p<0.01 Tg-pABri and
Tg-Combined versus
Tg-Control and Tg-Aß1-30KK
ns Tg-Control versus Tg-Aß1-30KK and
ns Tg-pABri versus Tg-Combined

FIG. 4A p<0.0001 one way ANOVA
post-hoc: p<0.001 Tg-pABri and
Tg-Combined versus
Tg-Control and Tg-Aß1-30KK
ns Tg-Control versus Tg-Aß1-30KK and
ns Tg-pABri versus Tg-Combined

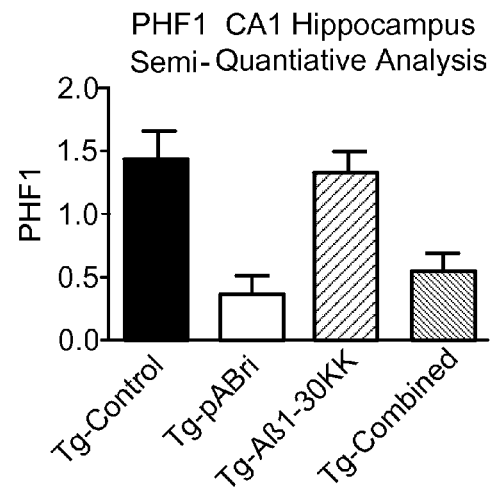

FIG. 4B

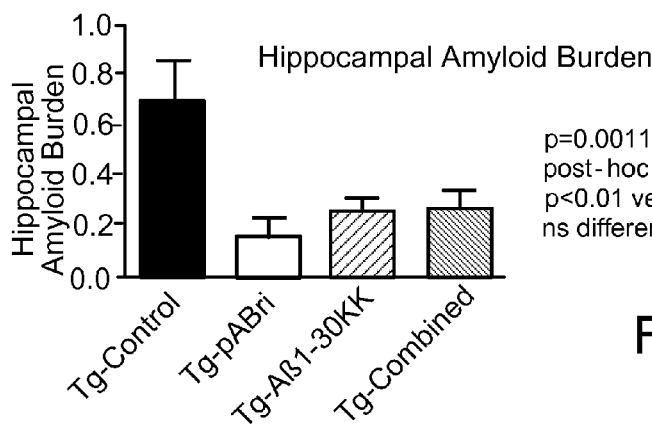

p=0.0011 by one way ANOVA
post-hoc testing: all treatment groups
p<0.01 versus control
ns difference between treatment groups

FIG. 4C

METHOD FOR TREATING AMYLOID DISEASE

CROSS REFERENCE TO RELATED APPLICATIONS

This application claims priority from U.S. Provisional Application Ser. No. 61/509,442, filed on Jul. 19, 2011, which is incorporated herein by reference in its entirety.

STATEMENT AS TO FEDERALLY SPONSORED RESEARCH

The United States Government has certain rights to this invention by virtue of funding reserved from Grant Nos. NS073501 and AG20245 from the National Institutes of Health.

FIELD OF THE INVENTION

The present invention relates to methods for treating amyloid diseases. Specifically, this invention relates to methods of reducing the levels of amyloid-beta (A$\beta$) peptides in bodily fluids by administration of A$\beta$ peptide immunogens capable of eliciting antibodies directed against A$\beta$.

BACKGROUND OF THE INVENTION

Amyloid diseases (disorders of protein folding), or amyloidoses, are characterized by the accumulation of a peptide, including the A$\beta$ peptide, existing as abnormal insoluble cross-$\beta$ sheet fibrils or amyloid deposits in the affected organs. Amyloid diseases include, but are not limited to, Alzheimer's disease, Lewy body dementia, type 2 diabetes, Huntington's disease, Parkinson's disease, and chronic inflammation. Amyloidosis is also a common and serious complication of long-term hemodialysis for end-stage renal failure. Amyloidosis—in which amyloid deposits are the direct cause of death is responsible for about one per thousand of all deaths in developed countries.

Alzheimer's disease (AD) is the most common form of late-life dementia in adults, constituting the sixth leading cause of death in the United States (see, e.g., Alzheimer's Association, 2012 Alzheimer's Disease Facts and Figures, Alzheimer's & Dementia, Volume 8, Issue 2, available at www.alz.org/downloads/facts_figures_2012.pdf). AD is also globally the most common cause of dementia; the increasing numbers of AD patients worldwide is one of the most pressing medical issues of the $21^{st}$ century (see, e.g., Alzheimer's Disease International World Alzheimer Report 2011, The benefits of early diagnosis and intervention, Martin Prince, Renata Bryce and Cleusa Ferri, Institute of Psychiatry, King's College London, UK, published by Alzheimer's Disease International (ADI), September 2011, available at www.alz.co.uk/research/world-report-2011). Approximately 5% of the population over 65 years old is affected by this progressive degenerative disorder that is characterized by memory loss, confusion and a variety of cognitive disabilities.

Neuropathologically, AD is characterized by four major lesions: a) intraneuronal, cytoplasmic deposits of neurofibrillary tangles (NFT), b) parenchymal amyloid deposits called neuritic plaques, c) cerebrovascular amyloidosis, and d) synaptic and neuronal loss. One of the key events in AD is the deposition of amyloid as insoluble fibrous masses (amyloidogenesis) resulting in extracellular neuritic plaques and deposits around the walls of cerebral blood vessels. The major constituent of the neuritic plaques and congophilic angiopathy is A$\beta$, although these deposits also contain other proteins such as glycosaminoglycans and apolipoproteins. The major constituent of NFTs is the tau protein in an abnormal conformation which is hyperphosphorylated. NFTs are also considered amyloid deposits, wherein tau (pTau) is present in toxic oligomeric forms that might or might not be soluble. Hence, in AD two different biochemical types of proteins are deposited and at least two major protein toxic oligomeric forms are involved.

A$\beta$ is a 4.14.3 kD hydrophobic peptide that is encoded on chromosome 21 as part of a much longer amyloid precursor protein APP (Muller-Hill et al., Nucleic Acids Res 1989; 17:517-522). The APP protein starts with a leader sequence (signal peptide), followed by a cysteine-rich region, an acidic-rich domain, a protease inhibitor motif, a putative N-glycosylated region, a transmembrane domain, and finally a small cytoplasmic region. The A$\beta$ sequence begins close to the membrane on the extracellular side and ends within the membrane. Two-thirds of A$\beta$ faces the extracellular space, and the other third is embedded in the membrane (Kang et al., Nature 1984; 325:733-736, Dyrks et al., EMBO J. 1988; 7:949-957). Several lines of evidence suggest that amyloid may play a central role in the early pathogenesis of AD (Soto et al., 1994; 63:1191-1198).

Evidence that amyloid may play an important role in the early pathogenesis of AD comes primarily from studies of individuals affected by the familial form of AD (FAD) or by Down's syndrome. Down's syndrome patients have three copies of the APP gene and develop AD neuropathology at an early age (Wisniewski et al., Ann Neurol 1985; 17:278-282). Genetic analysis of families with hereditary AD revealed mutations in chromosome 21, near or within the A$\beta$ sequence (Ghiso et al., Adv. Drug Deliv. Rev. 2002; 54(12):1539-51), in addition to mutations within the presenilin 1 and 2 genes. Moreover, it was reported that transgenic mice expressing high levels of human mutant APP progressively develop amyloidosis in their brains (Games et al., Nature 1995; 373:523-527). These findings appear to implicate amyloidogenesis in the pathophysiology of AD. In addition, A$\beta$ fibrils are toxic to neurons in culture, and to some extent when injected into animal brains (Sigurdsson et al., Neurobiol Aging 1996; 17:893-901; Sigurdsson et at, J Neuropathol Exp Neurol. 1997; 56:714-725).

Furthermore, several other pieces of evidence suggest that the deposition of A$\beta$ is a central triggering event in the pathogenesis of AD, which subsequently might be linked or related to NFT formation and neuronal loss. The amyloid deposits in AD share a number of properties with all the other cerebral amyloidoses, such as the prion related amyloidoses, as well as the systemic amyloidoses. These characteristics are: 1) being relatively insoluble; 2) having a high degree of $\beta$-sheet secondary structure, which is associated with a tendency to aggregate or polymerize; 3) ultrastructurally, the deposits are mainly fibrillary; 4) the presence of certain amyloid-associating proteins such as amyloid P component, proteoglycans and apolipoproteins; and 5) deposits show a characteristic apple-green birefringence when viewed under polarized light after Congo red staining.

The same peptide that forms amyloid deposits in the AD brain was also found in a soluble form (sA$\beta$) normally circulating in human body fluids (Seubert et al., Nature 1992; 359:325-327; Shoji et al., Science 1992; 258:126-129). sA$\beta$ was reported to pass freely from the brain to the blood (Ji et al., Journal of Alzheimer's Disease 2001; 3:23-30; Shibata et al., J Clin Invest 2000; 106: 1489-99; Ghersi-Egea et al., J Neurochem 1996; 67(2):880-3; Zlokovic et al., Biochem Biophys Res Commun 1994; 205:1431-1437), reported that the blood-brain barrier (BBB) has the capability to control cerebrovascular sequestration and transport of circulating sAβ, and that the transport of sAβ across the BBB was significantly increased in guinea pigs when sAβ was perfused as a complex with apolipoprotein J (apoJ). The sAβ-apoJ complex was found in normal cerebrospinal fluid (CSF; Ghiso et al., Biochem J 1993; 293:27-30; Ghiso et al., Mol Neurobiol 1994; 8:49-64) and in vivo studies indicated that sAβ is transported with apoJ as a component of the high density lipoproteins (HDL) in normal human plasma (Koudinov et al., Biochem Biophys Res Commun 1994; 205:1164-1171). It was also reported by (Zlokovic et al., Proc Natl Acad Sci USA 1996; 93:4229-4234), that the transport of sAβ from the circulation into the brain was almost abolished when the apoJ receptor, gp330, was blocked. It has been suggested that the amyloid formation is a nucleation-dependent phenomena in which the initial insoluble "seed" allows the selective deposition of amyloid (Jarrett et al., Cell 1993; 73:1055-1058; Jarrett et al., Biochemistry 1993; 32:4693-4697).

Therapeutic strategies proposed for treating AD and other amyloid diseases include the use of compounds that affect processing of the amyloid-β precursor protein (Dovey et al., J. Neurochem. 2001; 76:173-182), or that interfere with fibril formation or promote fibril disassembly (Soto et al., Nat Med 1998; 4:822-826; Sigurdsson et al., J Neuropath Exp Neurol 2000; 59:11-17; Findeis M A., Biochim Biophys Acta 2000; 1502:76-84), as well as the administration of Aβ antibodies to disassemble fibrillar Aβ, maintain Aβ solubility and to block the toxic effects of Aβ (Frenkel et al, J Neuroimmunol 1999; 95:136-142). However, recently a Phase II clinical trial using a vaccination approach where Aβ1-42 was injected into individuals in the early stages of AD was terminated because of cerebral inflammation observed in some patients.

Taken together, despite some advances in the art, to date, there is no cure or effective therapy for reducing a patient's amyloid burden or preventing amyloid deposition in AD and other amyloid diseases. Thus, there exists a need in the art for developing effective methods for reducing a patient's amyloid burden.

SUMMARY OF THE INVENTION

The present invention is based, in part, on the discovery that amyloid diseases can be treated by the administration of immunogenic modified Aβ peptides that elicit antibodies directed against a particular conformation of Aβ in order to bind to Aβ in organs (e.g., brain) and/or bodily fluids.

Although the primary sequence of Aβ and tau has no homology, the abnormal conformation of both these proteins when deposited as amyloid plaques and NFTs or in soluble and semi-soluble Aβ oligomers, is similar. Hence, the present inventors have further hypothesized that a treatment that is directed against the abnormal conformation of Aβ in amyloid plaques and/or in soluble and semi-soluble Aβ oligomers may also directly reduce NFT-related pathology.

The administration of immunogenic modified Aβ peptides of the present invention leads to the reduction of a patient's amyloid burden and the reduction in Aβ and/or pTau oligomers in bodily fluids and/or affected organs.

Thus, in one aspect, the invention provides immunogenic modified Aβ peptides, which peptides are soluble, non-fibrillogenic, contain Lysine substitutions in amino acid positions corresponding to amino acids 18 and 19 of Aβ1-42, and have the property of eliciting antibodies directed against the abnormal conformation of Aβ in amyloid plaques and/or in soluble and semi-soluble Aβ oligomers.

The present invention also provides various conjugated and fusion forms of said immunogenic modified Aβ peptides, which conjugated and fusion forms are capable of eliciting antibodies directed against the abnormal conformation of Aβ in amyloid plaques and/or in soluble and semi-soluble Aβ oligomers.

The invention also provides polymerized forms of said immunogenic modified Aβ peptides, which polymerized forms have molecular weight less than 100 kDa and are capable of eliciting antibodies directed against the abnormal conformation of Aβ in amyloid plaques and/or in soluble and semi-soluble Aβ oligomers. Such polymerized forms can be produced using methods known in the art (such as, e.g., by a reaction with a cross linking reagent [e.g., glutaraldehyde or 1-Ethyl-3-[3-dimethylaminopropyl]carbodiimide hydrochloride (EDC)] or by cysteine oxidation-induced disulfide cross-linking). In one embodiment, such polymerized forms are produced using controlled polymerization with glutaraldehyde as described in U.S. Patent Appl. Publ. No. 2010/0284909 and Goni et al., PLoS One, 2010, 5(10): e13391.

Non-limiting examples of the immunogenic modified Aβ peptides of the present invention include Aβ 1-30 $K_{18}K_{19}$ (DAEFRHDSGYEVHHQKLKKFAEDVGSNKGA; SEQ ID NO: 1), Aβ 1-40 $K_{18}K_{19}$ (DAEFRHDSGYEVHHQKLKKFAEDVGSNKGAIIGLMVGGVV; SEQ ID NO: 2), Aβ 1-42 $K_{18}K_{19}$ (DAEFRHDSGYEVHHQKLKKFAEDVGSNKGAIIGLMVGGVVIA; SEQ ID NO: 3), Aβ 1-20 $K_{18}K_{19}$ (DAEFRHDSGYEVHHQKLKKF; SEQ ID NO: 4), Aβ 10-30 $K_{18}K_{19}$ (YEVHHQKLKKFAEDVGSNKGA; SEQ ID NO: 5), Aβ 10-40 $K_{18}K_{19}$ (YEVHHQKLKKFAEDVGSNKGAIIGLMVGGVV; SEQ ID NO: 6), and Aβ 10-42 $K_{18}K_{19}$ (YEVHHQKLKKFAEDVGSNKGAIIGLMVGGVVIA; SEQ ID NO: 7).

The invention also provides pharmaceutical compositions comprising one or more of the immunogenic modified Aβ peptides and/or polymerized forms of the invention and a pharmaceutically acceptable carrier or diluent. In one embodiment, the pharmaceutical composition further comprises an adjuvant. In another embodiment, the pharmaceutical composition further comprises a polymerized British amyloidosis related peptide (pABri) (e.g., as described in U.S. Patent Appl. Publ. No. 2010/0284909 and Goni et al., PLoS One, 2010, 5(10): e13391). In one embodiment, the monomer of the pABri peptide has the sequence CSRTVKKNIIEEN (SEQ ID NO: 8).

In conjunction with the immunogenic modified Aβ peptides and pharmaceutical compositions, the present invention also provides a method of treating a patient (e.g., human) suffering from an amyloid disease (e.g., Alzheimer's disease, Lewy Body Dementia, Frontotemporal dementia, type 2 diabetes, Huntington's disease, Parkinson's disease, amyloidosis associated with hemodialysis for renal failure, Down syndrome, hereditary cerebral hemorrhage with amyloidosis, kuru, Creutzfeldt-Jakob disease, Gerstmann-Straussler-Scheinker disease, fatal familial insomnia, British familial dementia, Danish familial dementia, familial corneal amyloidosis, Familial corneal dystrophies, medullary thyroid carcinoma, insulinoma, isolated atrial amyloidosis, pituitary amyloidosis, aortic amyloidosis, plasma cell disorders, familial amyloidosis, senile cardiac amyloidosis, inflammation-associated amyloidosis, familial Mediterranean fever, systemic amyloidosis, and familial systemic amyloidosis) or a tauopathy (e.g., Frontotemporal dementia, chronic traumatic encephalopathy, progressive supranuclear palsy, corticobasal degeneration) comprising administering to the patient a therapeutically effective amount of one or more peptides (and/or polymerized forms thereof) of the invention (or administering a pharmaceutical composition comprising such peptide(s) and/or polymerized forms thereof). In one specific embodiment, the peptide is Aβ 1-30 $K_{18}K_{19}$ (SEQ ID NO: 1). In another specific embodiment, two or more different peptides and/or polymerized forms thereof are administered. In one specific embodiment, the peptide(s) of the invention (or polymerized forms thereof) is administered in combination with a polymerized British amyloidosis related peptide (pABri). Useful pABri peptides are described, for example, in U.S. Patent Appl. Publ. No. 2010/0284909 and Goni et al., PLoS One, 2010, 5(10): e13391. In one embodiment, the monomer of the pABri peptide has the sequence CSRTVKKNIIEEN (SEQ ID NO: 8).

In one embodiment, the treatment method of the invention further comprises administering an adjuvant.

In one embodiment, the peptide of the invention (or polymerized forms thereof) is administered systemically (e.g., intramuscularly, subcutaneously, orally, or intranasally).

In one embodiment, the therapeutically effective amount of the peptide (or polymerized forms thereof) is between about 0.1 mg and about 20 mg per kg body weight of the patient per day.

In one embodiment, the patient's blood-brain-barrier (BBB) is permeabilized prior to administration of the peptide (e.g., by administering insulin growth factor I (IGF-I)).

These and other aspects of the present invention will be apparent to those of ordinary skin in the art in the following description, claims and drawings.

BRIEF DESCRIPTION OF THE DRAWINGS

FIGS. 4A-C are bar graphs showing immunohistological analysis in 3×Tg mice immunized with Aβ 1-30 $K_{18}K_{19}$ peptide (Aβ1-30KK) (SEQ ID NO: 1), vehicle control, polymerized British amyloidosis related peptides (pABri) (monomer sequence SEQ ID NO: 8), or a combination of Aβ1-30KK and pABri. Panels A and B show the PHF-1 immunohistochemical quantitation in the cortex (A) and CA1 hippocampus (B). Panel C shows the amyloid burden in the hippocampus. All treated mice demonstrate a clear reduction in the amyloid burden compared to controls.

DETAILED DESCRIPTION OF THE INVENTION

Figure 1A:
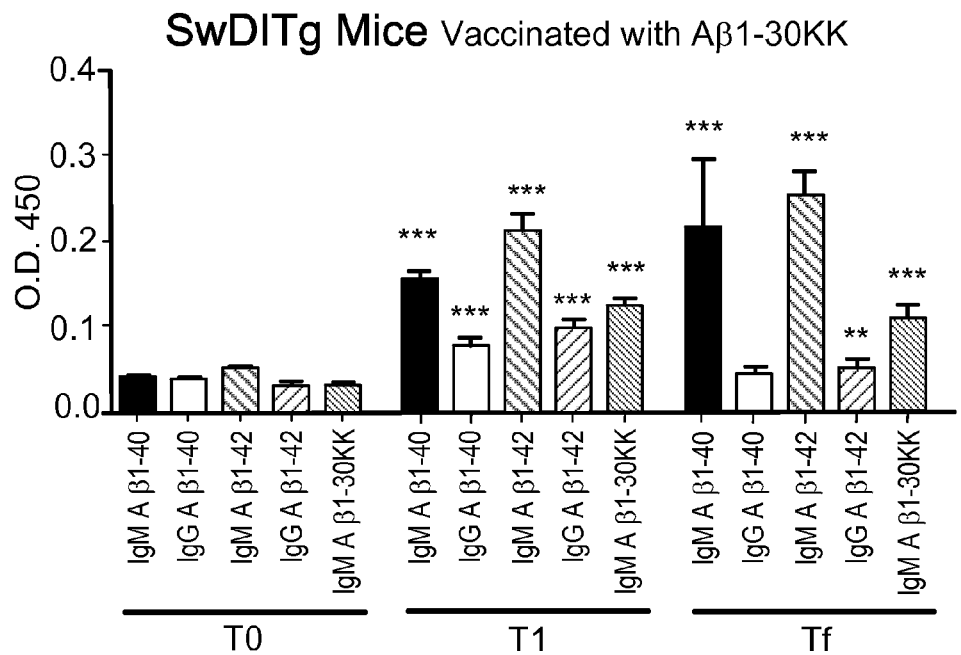
FIGS. 1A-1D are graphs showing the antibody titers of IgM and IgG cross-reactive with Aβ1-40 and Aβ1-42 at T0, T1 (after the 6th inoculation) and Tf (at the time of sacrifice) (*p<0.001; p<0.01; *p>0.05 versus T0) of TgSwDI (A) and 3×Tg (B-D) mice immunized with Aβ 1-30 $K_{18}K_{19}$ peptide (Aβ1-30KK) (SEQ ID NO: 1) (A, B), vehicle control (C), or a combination of Aβ1-30KK and polymerized British amyloidosis related peptides (pABri) (monomer sequence SEQ ID NO: 8) (D).
Figure 1B:
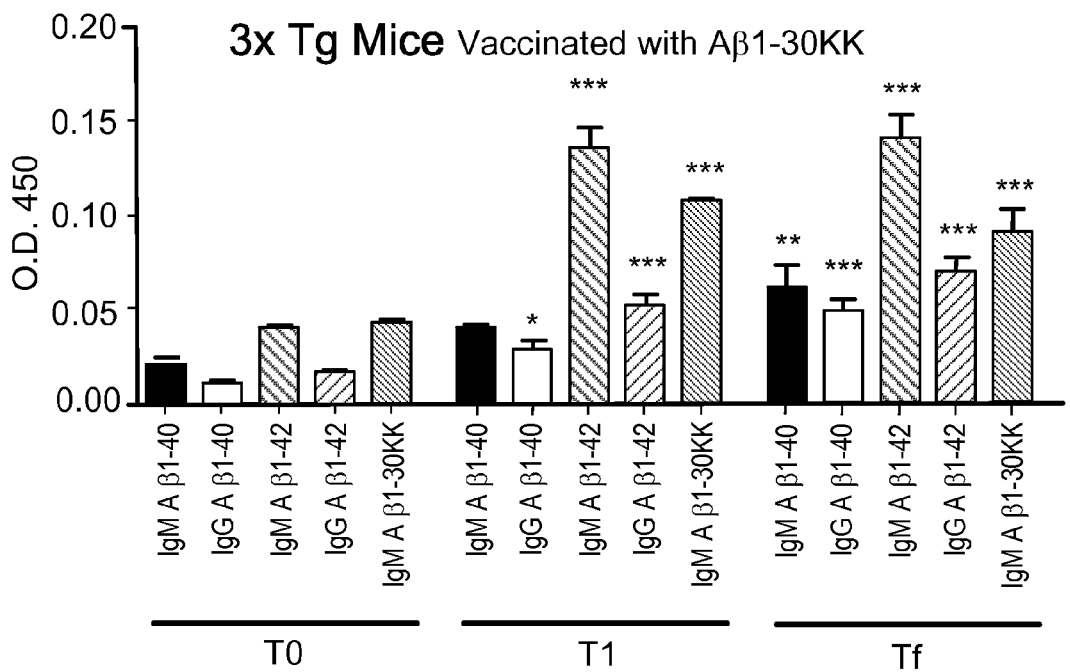
Figure 1C:
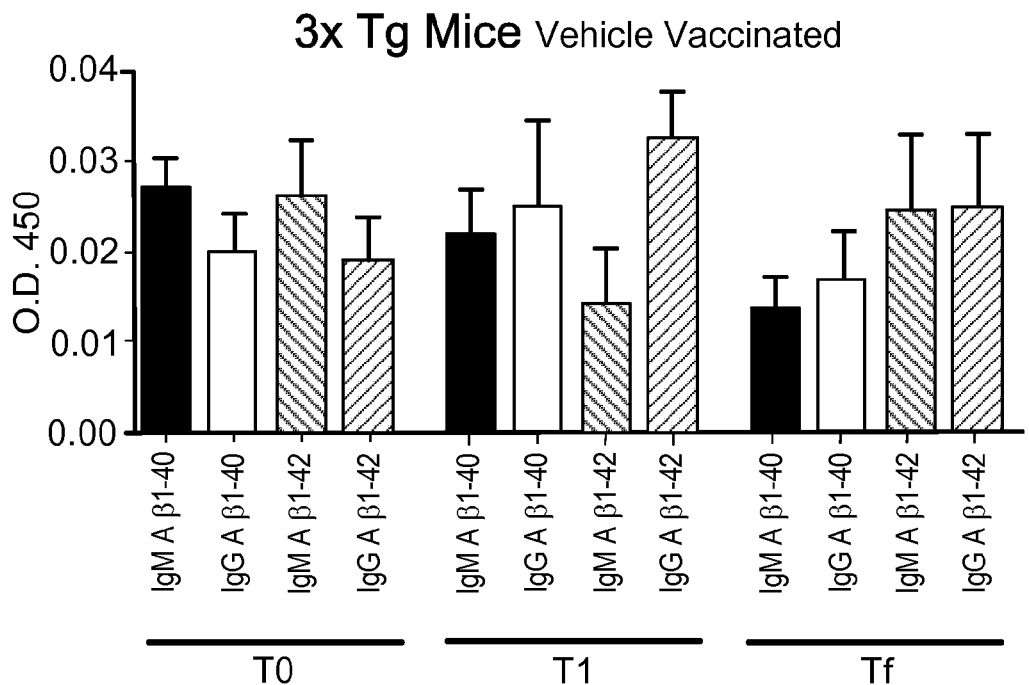
Figure 1D:
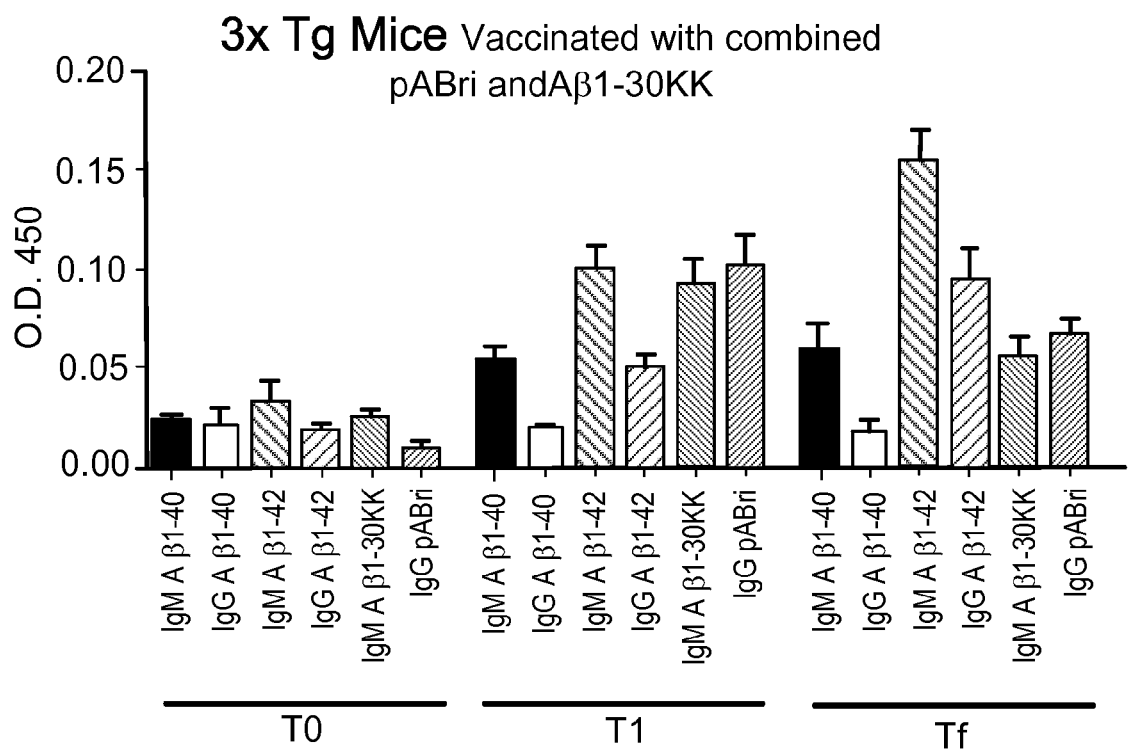

The present invention provides a method for removing deposited, oligomeric and soluble amyloid β, including Aβ1-40 and Aβ1-42 from bodily fluids and organs. The present invention also provides a method for removing toxic pTau oligomers in an abnormal conformation from bodily fluids and organs.

The efficacy of the treatment of the invention can be determined by evaluating the Alzheimer's Disease (AD) symptoms of the patient and/or by measuring the Aβ concentration in bodily fluids or organs (e.g., the patient's blood). Blood Aβ peptide measurements can be conducted using any method known in the art. For example, blood Aβ peptide measurements can involve taking a blood sample, separating serum from red blood cells, and using radioimmunoassay, enzyme linked immunosorbent assay (ELISA) or chromatographic analysis of the Aβ peptide contents in serum.

The subject or patient to which the present invention may be applicable can be any vertebrate species, preferably mammalian, including but not limited to, cows, horses, sheep, pigs, fowl (e.g., chickens), goats, cats, dogs, hamsters, mice, rats, rabbits, monkeys, chimpanzees, and humans. In a preferred embodiment, the subject is a human. The invention is particularly applicable for human subjects at risk for or suffering from Alzheimer's Disease (AD). However, the invention is also applicable for treatment of other amyloid diseases (such as, e.g., Lewy Body Dementia, Frontotemporal dementia, type 2 diabetes, Huntington's disease, Parkinson's disease, amyloidosis associated with hemodialysis for renal failure, Down syndrome, hereditary cerebral hemorrhage with amyloidosis, kuru, Creutzfeldt-Jakob disease, Gerstmann-Straussler-Scheinker disease, fatal familial insomnia, British familial dementia, Danish familial dementia, familial corneal amyloidosis, Familial corneal dystrophies, medullary thyroid carcinoma, insulinoma, isolated atrial amyloidosis, pituitary amyloidosis, aortic amyloidosis, plasma cell disorders, familial amyloidosis, senile cardiac amyloidosis, inflammation-associated amyloidosis, familial Mediterranean fever, systemic amyloidosis, and familial systemic amyloidosis) or a tauopathy (e.g., Frontotemporal dementia, chronic traumatic encephalopathy, progressive supranuclear palsy, corticobasal degeneration).

As used herein, "treat" or "treatment" generally refers to a reduction in the concentration or amount of Aβ peptide or toxic pTau oligomers in a bodily fluid and/or organ, including, but not limited to, the administration of peptides capable of inducing an immune response in vivo directed against deposited, oligomeric and/or soluble amyloid β (Aβ, including Aβ1-40 and Aβ1-42) and/or toxic pTau oligomers in bodily fluids and/or organs. "Treatment" also includes prophylactic treatment to those at risk for amyloid diseases, e.g., familial AD.

The term "bodily fluid" as used herein includes blood, plasma, serum, cerebroventricular fluid (CVF), cerebrospinal fluid, and other extracellular or interstitial fluids in the body of a subject.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A practical Approach*, Volumes I and II (D. N. Glover ed. 1985); *Oligonucleotide Synthesis* (M J. Gait ed. 1984); *Nucleic Acid Hybridization* (B. D. Hames & S. J. Higgins eds. (1985>>; *Transcription and Translation* (B. D. Hames & S. J. Higgins, eds. (1984>>; *Animal Cell Culture* (R. I. Freshney, ed. (1986>>; *Immobilized Cells and Enzymes* (IRL Press, (1986>>; B. Perbal, *A practical Guide To Molecular Cloning* (1984); F. M. Ausubel et al. (eds.), *Current Protocols in Molecular Biology*, John Wiley & Sons, Inc. (1994).

As used herein, the term "isolated" means that the referenced material is removed from its native environment, e.g., a cell. Thus, an isolated biological material can be free of some or all cellular components (e.g., cytoplasmic or membrane component). A material shall be deemed isolated if it is present in a cell extract or in a heterologous cell. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated, e.g., by chromatography, gel electrophoresis, immunoassay, composition analysis, biological assay, and other methods known in the art.

Methods for purification are well-known in the art. For example, nucleic acids can be purified by precipitation, chromatography (including, without limitation, preparative solid phase chromatography, oligonucleotide hybridization, and triple helix chromatography), ultracentrifugation, and other means. Peptides and proteins can be purified by various methods including, without limitation, preparative disc-gel electrophoresis and isoelectric focusing; affinity HPLC, reversed-phase HPLC, gel filtration or size exclusion, ion exchange and partition chromatography; precipitation and salting-out chromatography; extraction; and countercurrent distribution. For some purposes, it is preferable to produce a peptide or protein in a recombinant system in which said peptide or protein may contain an additional sequence tag that facilitates purification, such as, but not limited to, a polyhistidine sequence, or a sequence that specifically binds to an antibody, such as FLAG and GST. The resulting tagged peptide or protein can then be purified from a crude lysate of the host cell by chromatography on an appropriate solid-phase matrix. Alternatively, antibodies produced against the peptide or protein (or against peptides derived therefrom) can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting (FAS)). Other purification methods are possible and contemplated herein. A purified material may contain less than about 50%, preferably less than about 75%, and most preferably less than about 90%, of the cellular components, media, proteins, or other nondesimble components or impurities (as context requires), with which it was originally associated. The term "substantially pure" indicates the highest degree of purity which can be achieved using conventional purification techniques known in the art.

Immunigenic Modified Amyloid Beta (AB) Peptides of the Invention

Non-limiting examples of immunogenic modified Aβ peptides for use in the present invention are as follows:

TABLE 1

List of Exemplified Peptides of the Invention

| Peptide Name | SEQ ID NO | Sequence |
|---|---|---|
| Aβ 1-30 $K_{18}K_{19}$ | 1 | DAEFRHDSGYEVHHQKLKKFAEDVGSNKGA |
| Aβ 1-40 $K_{18}K_{19}$ | 2 | DAEFRHDSGYEVHHQKLKKFAEDVGSNKGAIIGLMVGGVV |
| Aβ 1-42 $K_{18}K_{19}$ | 3 | DAEFRHDSGYEVHHQKLKKFAEDVGSNKGAIIGLMVGGVVIA |
| Aβ 1-20 $K_{18}K_{19}$ | 4 | DAEFRHDSGYEVHHQKLKKF |
| Aβ 10-30 $K_{18}K_{19}$ | 5 | YEVHHQKLKKFAEDVGSNKGA |
| Aβ 10-40 $K_{18}K_{19}$ | 6 | YEVHHQKLKKFAEDVGSNKGAIIGLMVGGVV |
| Aβ 10-42 $K_{18}K_{19}$ | 7 | YEVHHQKLKKFAEDVGSNKGAIIGLMVGGVVIA |

The present invention also encompasses various additional immunogenic modified Aβ peptides having substitutions in amino acid positions corresponding to amino acids 18 and 19 of Aβ1-42, which peptides are soluble non-fibrillogenic and are capable of eliciting antibodies directed against the abnormal conformation of Aβ in amyloid plaques and/or in soluble and semi-soluble Aβ oligomers.

The immunogenic modified Aβ peptides of the invention can be synthesized using techniques well known to those of ordinary skill in the art (see, e.g., SYNTHETIC PEPTIDES: A USERS GUIDE 93-210 (Gregory A. Grant ed., 1992)) or can be purchased from numerous commercial sources such as, e.g., the W. M. Keck Biotechnology Resource Laboratory, Yale University, 300 George Street, New Haven, Conn. 06511.

To enhance immunogenicity, the peptide of the invention can be linked in-frame to an adjuvant polypeptide. The adjuvant polypeptide can be any adjuvant polypeptide known in the art, including, but not limited to, cholera toxin B, flagellin, human papillomavirus L1 or L2 protein, herpes simplex glycoprotein D (gD), complement C4 binding protein, TL4 ligand, and IL-1.beta. The peptide may be linked directly to the adjuvant polypeptide or coupled to the adjuvant by way of a short linker sequence. Suitable linker sequences include glycine or serine-rich linkers described supra or other flexible immunoglobulin linkers as disclosed, e.g., in U.S. Pat. No. 5,516,637.

Alternatively or in addition, the peptide of the invention can be conjugated to an immunogenic carrier molecule. The immunogenic carrier molecule can be covalently or non-covalently bonded to the peptide. Suitable immunogenic carrier molecules include, but are not limited to, serum albumins, chicken egg ovalbumin, keyhole limpet hemocyanin, tetanus toxoid, thyroglobulin, pneumococcal capsular polysaccharides, CRM 197, immunoglobulin molecules, attenuated Salmonella, and meningococcal outer membrane proteins. Other suitable immunogenic carrier molecules include T-cell epitopes, such as tetanus toxoid (e.g., the P2 and P30 epitopes), Hepatitis B surface antigen, pertussis, toxoid, diphtheria toxoid, measles virus F protein, *Chlamydia trachomatis* major outer membrane protein, *Plasmodium falciparum* circumsporozite T, *P. falciparum* CS antigen, *Schistosoma mansoni* triose phosphate isomersae, *Escherichia coli* TraT, and Influenza virus hemagluttinin (HA). Other suitable immunogenic carrier molecules include promiscuous T helper cell epitopes which are derived from hepatitis B virus, *Bordetella pertussis*, *Clostridium tetani*, *Pertusaria trachythallina*, *E. coli*, *Chlamydia trachomatis*, *Diphtheria*, *P. falciparum*, and *Schistosoma mansoni* (see, e.g., U.S. Pat. No. 6,906,169; U.S. Pat. Appl. Publ. No. 20030068325; Int. Appl. Publ. Nos. WO/2002/096350 and WO01/42306).

Techniques for linking a peptide to an immunogenic carrier molecule include chemical crosslinking by, e.g., formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine residues on one protein, and an amide linkage through the epsilon-amino on a lysine, or other free amino group in other amino acids. A variety of such disulfide/amide-forming agents are described by Jansen et al., Immun Rev 62:185-216 (1982). Other bifunctional coupling agents form a thioether rather than a disulfide linkage. Many of these thio-ether-forming agents are commercially available and include reactive esters of 6-maleimidocaproic acid, 2-bromoacetic acid, 2-iodoacetic acid, and 4-(N-maleimido-methyl)cyclohexane-1-carboxylic acid. The carboxyl groups can be activated, e.g., by combining them with succinimide or 1-hydroxyl-2-nitro-4-sulfonic acid, sodium salt.

The invention also provides polymerized forms of the above peptides, which polymerized forms have molecular weight less than 100 kDa and are capable of eliciting antibodies directed against the abnormal conformation of Aβ in amyloid plaques and/or in soluble and semi-soluble Aβ oligomers. Such polymerized forms can be produced using methods known in the art. For example, the peptide can be polymerized by a reaction with a cross linking reagent. Suitable cross-linking reagents include, but are not limited to glutaraldehyde and 1-Ethyl-3-[3-dimethylaminopropyl]carbodiimide hydrochloride (EDC). Alternatively, the peptide can be polymerized by cysteine oxidation induced disulfide cross linking.

In one embodiment, polymerized forms can be produced using controlled polymerization with glutaraldehyde as described in U.S. Patent Appl. Publ. No. 2010/0284909 and Goni et al., PLoS One, 2010, 5(10): e13391. Briefly, this method involves dissolving the peptide at 3 mg/ml, in 100 mM borate buffer saline (BBS), pH 7.4; preparing fresh 1% glutaraldehyde in BBS and adding glutaraldehyde to the peptide to a final 5 mM glutaraldehyde concentration, followed by incubation in an Eppendorf block at 800 rpm at 56° C. for 16 hrs. The solution is then quenched with 0.5 M glycine to make the solution 100 mM in glycine. After five minutes the solution is diluted 1:3 with BBS, dialyzed against 2 mM BBS overnight at 4° C., aliquoted, and lyophilized. To determine the degree of aggregation, the original monomeric peptide and polymerized peptide are electrophoresed on 12.5% SDS-polyacrylamide Tris-tricine gels under reducing conditions and the peptides are detected by immunoblotting with peptide-specific antibodies. The secondary structure of the polymerized immunogens can be evaluated using circular dichroism (CD) and electron microscopy as described previously (Sadowski et al., Proc Natl Acad Sci USA, 2006, 103:18787-18792).

Pharmaceutical Compositions and Administration

The present invention also provides pharmaceutical compositions of the immunogenic modified Aβ peptides described herein. Such pharmaceutical compositions can be administered systemically. The term "systemic" as used herein includes parenteral, topical, transdermal, oral, by inhalation/pulmonary, rectal, nasal, and buccal administration. The term "parenteral" as used herein includes subcutaneous, intradermal, intravenous, intramuscular, intracranial, and intraperitoneal administration. Preferably, the peptides are administered intramuscularly, subcutaneously, orally, or intranasally in therapeutically effective amounts to treat amyloid diseases.

Mucosal immunization using the peptides of the invention can be effective to treat the encompassed pathologies (see, e.g., Goni et al., Neurosci., 2005, 133:413-421 and Goni et al., Neurosci., 2008, 153:679-686). In some embodiments, for oral immunization, the immunogen can be administered as a conjugate with cholera toxin B (CTB) subunit. Cholera toxin augments the local (gastrointestinal) and systemic serum antibody response to co-administered antigens via a Th2 cell dependent pathway (Gelinas et al., Proc Natl Acad Sci USA, 2004, 101:14657-14662).

Optimization of pharmaceutical compositions and peptide immunization protocols can be first conducted in one or more animal models of AD or other amyloid diseases. Behavioral studies can include the radial arm maze analysis, locomotor activity and spatial learning (Sigurdsson et al., J. Neurosci., 2004, 24:6277-6282 and Sadowski et al., J Neuropath Exp Neurol, 2004, 63:418-428). Amyloid and tau burden quantitation, including biochemical levels for both soluble and insoluble Aβ, as well as, Aβ oligomer levels can be performed following previously published protocols (Sadowski et al., Proc Natl Acad Sci USA, 2006, 103:18787-18792 and Scholtzova et al., J Neurosci Res, 2008, 86:2784-2791).

The invention encompasses pharmaceutical compositions comprising therapeutically effective amounts of Aβ peptides together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), antioxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used, and this may have the effect of promoting sustained duration in the circulation. Such compositions may influence the physical state, stability, rate of in vivo release, and rate of in vivo clearance of the present peptides and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder, such as lyophilized form. Implantable sustained release formulations are also contemplated, as are transdermal formulations.

Pharmaceutically acceptable carriers include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. PEG may be used (even apart from its use in derivatizing the peptide or analog). Dextrans, such as cyclodextran, may be used. Bile salts and other related enhancers may be used. Cellulose and cellulose derivatives may be used. Amino acids may be used, such as use in a buffer formulation.

Also, the use of liposomes, microcapsules or microspheres, inclusion complexes, or other types of carriers known in the art, is contemplated.

The pharmaceutical compositions of the present invention can further comprise an adjuvant. One class of useful adjuvants includes aluminum salts, such as aluminum hydroxide, aluminum phosphate, or aluminum sulfate. Such adjuvants can be used with or without other specific immunostimulating agents such as MPL or 3-DMP, QS-21, flagellin, polymeric or monomeric amino acids such as polyglutamic acid or polylysine, or pluronic polyols. Oil-in-water emulsion formulations are also suitable adjuvants that can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2' dipalmitoyl-sn-1-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™, or other bacterial cell wall components). A suitable oil-in-water emulsion is MF59 (containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.) as described in Int. Appl. Publ. No. WO90/14837. Other suitable oil-in-water emulsions include SAF (containing 10% Squalene, 0.4% Tween 80, 5% pluronic-blocked polymer L121, and thr-MDP, either microfluidized into a submicron emulsion or vortexed to generate a larger particle size emulsion) and Ribi™ adjuvant system (RAS; containing 2% squalene, 0.2% Tween 80, and one or more bacterial cell wall components). Another class of preferred adjuvants is saponin adjuvants, such as Stimulon™ (QS-21) or particles generated therefrom such as ISCOMs (immunostimulating complexes) and ISCOMATRIX. Other suitable adjuvants include incomplete or complete Freund's Adjuvant (IFA), cytokines, such as interleukins (IL-1, IL-2, and IL-12), macrophage colony stimulating factor (M-CSF), lysolecithin, tumor necrosis factor (TNF), and liposome polycation DNA particles. Such adjuvants are generally available from commercial sources.

The pharmaceutical compositions of the invention can further comprise agents which facilitate brain delivery. Non-limiting examples of such useful agents include, e.g., functionalized nanocarriers (e.g., nanoparticles coated with transferrin or transferrin receptor [TR] antibodies) and liposomes (e.g., liposomes coated with targeting molecules such as antibodies, Trojan Horses Liposomes [THL]), antibodies (e.g., antibodies against transferrin receptor [TR] and insulin receptor [HIR], BBB transmigrating Llama single domain antibodies (sdAb)), chimeric peptides (e.g., Angiopeps derived from proteins expressing the Kunitz domain), low-density lipoprotein receptor related proteins 1 and 2 (LRP-1 and 2), diphtheria toxin receptor (DTR), mesenchyme stem cells, etc.

In Vivo Treatment

Treatment in vivo, i.e., by a method where an immunogenic modified Aβ peptide of the invention is administered to the patient, is expected to result in a reduced amyloid burden within the brain of an AD patient and has the potential to halt or slow the progression of the cognitive impairments observed in this disease. In other amyloid diseases, this treatment approach is expected to enhance clearance of the respective amyloid proteins from their target organs in a similar manner and therefore improve the condition of those patients.

Without wishing to be bound by any particular theory, it is believed that following administration of the immunogenic modified Aβ peptides of the invention, the induced antibodies will bind to Aβ. The Aβ is preferably, although not necessarily, soluble Aβ and is free, e.g., not irreversibly bound to an amyloid plaque or other component. Free Aβ includes, but is not limited to, circulating Aβ in blood; free Aβ in the interstitial fluid in the brain; and Aβ bound to a ligand such as a naturally occurring plasma protein, e.g., albumin or transthyretin. Normally, equilibrium is presumed to exist between free Aβ in circulation and Aβ within the brain or other affected organs. A reduction in free Aβ in the circulation by binding to Aβ antibodies induced by the immunogenic modified Aβ peptides of the present invention (which antibodies do not cross the blood-brain-barrier (BBB) or have a saturated uptake) can therefore result in an efflux of Aβ out of the brain or other affected organs to re-establish the equilibrium.

In one embodiment, the patient is treated in a manner so as to increase the selective permeability of the blood-brain barrier (BBB), allowing the transport of Aβ antibodies into the brain from the blood. Aβ bound to Aβ-binding antibodies may be shuttled out of the brain or may be degraded within the central nervous system. The net effect will be a reduced concentration of Aβ within the interstitial fluid. Treatments to selectively increase the permeability of the BBB in a patient include, but are not limited to, the administration of about 1 to about 1000 µg/kg body weight, preferably about 10 to about 100 µg/kg bodyweight, of IGF-I (e.g., as a bolus injection to a patient about 0.5 to 10 hours, preferably about 1 hour, before the Aβ peptide administration). Also, even without selective permeabilization with a drug such as IGF-I, the BBB may be compromised in AD so that Aβ-binding antibodies that normally do not enter the brain, or have a saturated uptake, may access the brain more readily. Hence, Aβ clearance mediated by these antibodies may be partially from within the brain.

The specific dosage regimen and amounts administered for the peptides of the present invention will be determined by the attending physician, considering various factors which modify the action of drugs, e.g. the age, condition, body weight, sex and diet of the patient, the disease state, other medications administered, and other clinical factors. An effective amount to treat the disease would broadly range (e.g., between about 0.1 mg and about 20 mg per kg body weight of the recipient per day), and may be administered as a single dose or divided doses. If needed, the treatments can be continued throughout the life of the patient.

Subjects amenable to treatment in accordance with the methods of the present invention include individuals at risk of developing an amyloid related disease but not showing symptoms, as well as subjects presently showing symptoms. Non-limiting examples of diseases subject to treatment include, e.g., Alzheimer's disease (AD), Lewy Body Dementia, Frontotemporal dementia, type 2 diabetes, Huntington's disease, Parkinson's disease, amyloidosis associated with hemodialysis for renal failure, Down syndrome, hereditary cerebral hemorrhage with amyloidosis, kuru, Creutzfeldt-Jakob disease, Gerstmann-Straussler-Scheinker disease, fatal familial insomnia, British familial dementia, Danish familial dementia, familial corneal amyloidosis, Familial corneal dystrophies, medullary thyroid carcinoma, insulinoma, isolated atrial amyloidosis, pituitary amyloidosis, aortic amyloidosis, plasma cell disorders, familial amyloidosis, senile cardiac amyloidosis, inflammation-associated amyloidosis, familial Mediterranean fever, systemic amyloidosis, familial systemic amyloidosis, chronic traumatic encephalopathy, progressive supranuclear palsy, and corticobasal degeneration.

The present methods and compositions are suitable for prophylactic treatment of individuals who have a known genetic risk of AD or another encompassed condition. Genetic markers associated with a risk of AD include, among others, mutations in the APP gene, particularly mutations at position 717 and positions 670 and 671 referred to as the Hardy and Swedish mutations, respectively. Other markers of AD risk include, e.g., mutations in the presenilin genes, PS1 and PS2, and ApoE4, family history of AD, hypercholesterolemia or atherosclerosis.

Treatment can be monitored and adjusted by assaying antibody, or activated T-cell or B-cell responses to the pathological peptides/proteins. Typically, repeated dosages are given if the immune response starts to fade.

The present invention is described below in working examples which are intended to further describe the invention without limiting the scope thereof.

EXAMPLE 1

Alzheimer's disease (AD) is the most common of the conformational neurodegenerative disorders. Current treatments for AD are largely symptomatic and minimally effective. Major problems with previous immunotherapeutic approaches include: potential of toxicity from autoimmune encephalitis, tau-related pathology not being addressed, and the need to effectively clear congophilic angiopathy (CAA).

The Aβ 1-42 peptide (DAEFRHDSGYEVHHQKLVF-FAEDVGSNKGAIIGLMVGGVVIA; SEQ ID NO: 9) and portions or variations of the same have been extensively used as immunogens for therapy of AD related pathology in animal models and in a few clinical trials. The results varied but only addressed the Aβ immunodominant epitopes, without targeting the toxic effect of oligomers, or reducing congophilic angiopathy (CAA).

Short Aβ sequences encompassing only 12 to 16 of the amino terminal residues proved to have some beneficial effects as immunogens for the therapy of amyloid related AD. However, these short sequence peptides do not have the proper configuration as found in pathologically oligomerized or fibrillized Aβ species. Use of these short peptides only allows detection of the amino terminus in a conformation not found in pathological Aβ species.

As disclosed herein, the present inventors have developed a novel immunomodulatory therapeutic approach that uses modified non-toxic non-fibrillogenic Aβ peptide Aβ 1-30 $K_{18}K_{19}$ (Aβ1-30KK; DAEFRHDSGYEVH-HQKLKKFAEDVGSNKGA; SEQ ID NO: 1) to overcome these limitations of vaccination. The $K_{18}K_{19}$ mutation is believed to give flexibility to the Aβ peptide structure and produce an immunogen with a cryptic epitope at the amino terminus. Such immunogen induces an immune response which is more targeted to toxic oligomeric and fibrillar Aβ species. As shown herein, immunization with the peptide Aβ 1-30 $K_{18}K_{19}$ can induce behavioral benefits in mice models of AD. Such behavioral benefits are associated with reductions in Aβ oligomers and an immune response that recognized aggregated Aβ. This approach has been tested herein in mice with both amyloid plaques and tangle pathology (3xTg mice; Oddo et al Neuron 2003; 39:409-21) and mice with extensive CAA related pathology/vascular amyloid deposits (TgSwDI; Davis et al JBC 2004; 279:20296-306).

Without wishing to be bound by any particular theory, it is hypothesized herein that the antibodies produced against Aβ 1-30 $K_{18}K_{19}$ and other immunogenic peptides of the invention would not only bind the Aβ peptides in a novel manner but will also alter their structure rendering the Aβ peptides non fibrillogenic/amyloidogenic, reversing their toxicity. The disappearance of the immunodominant epitope is expected to lower the risk of inducing self-toxicity and exacerbation of CAA.

Materials and Methods

Peptide.

Aβ 1-30 $K_{18}K_{19}$ (DAEFRHDSGYEVHHQKLKKFAED-VGSNKGA; SEQ ID NO: 1) was synthesized on an ABI 430A peptide synthesizer (AME Bioscience, Chicago, Ill.) at the Keck peptide synthesis facility at Yale University, CT, using a Vydac C18 preparative column, 2.5×30 cm (Vydac Separations, Hesperia, Calif.). Standard protocols for tBOC (tert-butyloxycarbonyl) chemistry were used. The peptide was subsequently cleaved from the resins using hydrofluoric acid and purified by high-pressure liquid chromatography (HPLC) on a Vydac C18 preparative column using linear gradients from 0-70% of acetonitrile in 0.1% trifluoroacetic acid. Mass spectroscopy of the lyophilized end-product was used to verify the expected molecular weight.

From the original sequence of the Aβ peptide only the first 30 amino acids were used to avoid fibrillogenic sequences at the carboyl-terminus; and two hydrophobic residues were mutated at positions 18 and 19 replacing Phenylalanine and Valine by two Lysine residues with epsilon amino groups that specifically give a particular secondary structure. These positively charged amino acids interfere with the expression of an immunodominant epitope and give flexibility to the middle structure of the molecule; hence, making available an otherwise cryptic epitope at the amino terminus of the peptide.

Animals.

3×Tg mice (Oddo et al Neuron 2003; 39:409-21) and TgSwDI mice (Davis et al JBC 2004; 279:20296-306) were used in the experiments. The animals were maintained on a 12-hour light-dark cycle, and had access to food and water ad libitum. The animal care was in accordance with institutional guidelines.

Immunization.

Starting at the age of 3 months, mice were immunized 4 times biweekly, subcutaneously with 50 µg peptide/animal in sterile saline:Alum (9:1), and thereafter 4 times bimonthly with 25 µg peptide/animal until the age of 12 months. At the age of 15-16 months the mice were subject to locomotor and cognitive behavioral testing (radial arm maze), followed by histological and biochemical analysis.

Antibody Levels.

IgM and IgG antibody titers cross-reactive with Aβ1-40 and Aβ1-42 were determined at at T0, T1 (after the 6th inoculation), and Tf (at the time of sacrifice) using an enzyme-linked immunosorbent assay (ELISA) as described previously (Jimenez-Huete et al., Alzheimers Reports 1998; 1:4147) in which Aβ or its derivative is coated onto microliter wells. The antibodies were detected by a goat anti-mouse IgG linked to a horseradish peroxidase (Amersham Pharmacia Biotech, Piscataway, N.J.) or a goat anti-mouse IgM peroxidase conjugate (Sigma, A8786), and tetramethyl benzidine (Pierce, Rockford, Ill.) was the substrate.

Radial Arm Maze Test (Behavioral Analysis).

Animals were kept in test room throughout the experiment, behind a cover to prevent view of the apparatus and room. Each animal underwent 2 days of adaptation, consisting of 15 minutes of maze exploration (2 subjects at a time), with 3 pieces of fruit loops in each arm. Subjects were exposed to arm doors only on day 2. Animals were food deprived 1 day before the first adaptation session and maintained at approximately ten percent body weight loss. Fruit loops were added to normal diet 5 days before deprivation schedule started. Animals entered and exited the apparatus through the center of the maze. Testing included recording correct and incorrect arms entered. Each trial was initiated by placing the mouse in the center of the maze and all doors into the arms were subsequently opened. After entry into an arm, the animal had to find and eat the reinforcer before the door was reopened to allow the animal to re-enter the center of the maze. Testing ended when all eight arms had been entered and reinforcers eaten. Re-entry into an arm constituted an error. Total number of errors and time to enter all eight arms were recorded. The animals were allowed access to food for up to 3-4 hours daily, depending on their body weight loss. The corners and holes in the maze were cleaned with 95% ethanol after each animal and the arms.

Histology.

Mice were sacrificed at 15-16 months of age after behavioral testing and their brains were processed for histology with subsequent stereological analysis. Mice were anesthetized with sodium pentobarbital (150 mg/kg, intraperitoneally), perfused transaortically with phosphate buffer and the brains processed as previously described (Sigurdsson et al., Neurobiol. Aging 1996; 17:893-901). The right hemisphere was immersion fixed in periodate-lysine-paraformaldehyde (PLP), whereas the left hemisphere was snap-frozen for measurements of Aβ levels using established ELISA methods (Mehta et al., Arch. Neurol. 2000; 57:100-105). Serial coronal sections (40 µm) were cut and every fifth section was stained with 6E10 which recognizes Aβ and stains both pre-amyloid and Aβ plaques (Kim et al., Neurosci Res Comm 1990; 7:113-122). After sectioning, the series were placed in ethylene glycol cryoprotectant and stored at −20° C. until used. Staining was performed as previously described (Sigurdsson et al., Neurobiol. Aging 1996; 17:893-901; Soto et al., Nat Med 1998; 4:822-826). Briefly, sections were incubated in 6E10 (provided by Richard Kascsak, Institute for Basic Research) primary antibody that selectively binds to human Aβ at a 1:1000 dilution. A mouse-on-mouse immunodetection kit (Vector Laboratories, Burlingame, Calif.) was used in which the anti-mouse IgG secondary antibody was used at a 1:2000 dilution. The sections were reacted in 3,3-diaminobenzidine tetrahydrochloride (DAB) with nickel ammonium sulfate (Ni; Mallinckrodt, Paris, Ky.) intensification.

Image Analysis.

Immunohistochemistry of tissue sections was quantified with a Bioquant image analysis system, and unbiased sampling was used (West et al., Trends Neurosci. 1999; 22:51-61). All procedures were performed by an individual blind to the experimental condition of the study. Cortical area analyzed was dorsomedially from the cingulate cortex and extended ventrolaterally to the rhinal fissure within the right hemisphere. The area of the grid was 800×800 $\mu m^2$ and amyloid load was measured in 20 frames per mouse (each: 640×480 $\mu m^2$), chosen randomly. The Aβ burden is defined as the percentage of area in the measurement field occupied by reaction product.

Results

Starting at the age of 3 months, 3×Tg and TgSwDI mice were immunized with Aβ 1-30 $K_{18}K_{19}$ (Aβ 1-30KK; DAE-FRHDSGYEVHHQKLKKFAEDVGSNKGA; SEQ ID NO: 1) peptide, Aβ 1-42 peptide (DAEFRHDSGYEVH-HQKLVFFAEDVGSNKGAIIGLMVGGVVIA; SEQ ID NO: 9), vehicle control, polymerized British amyloidosis related peptides (pABri) (monomer sequence CSRTVKKNI-IEEN; SEQ ID NO: 8), or a combination of Aβ 1-30 $K_{18}K_{19}$ and pABri, until the age of 12 months. At the age of 15-16 months the mice were subject to locomotor and cognitive behavioral testing (radial arm maze), followed by histological and biochemical analysis.

Locomotor testing showed no significant differences between all tested groups in both mice models.

Figure 2:
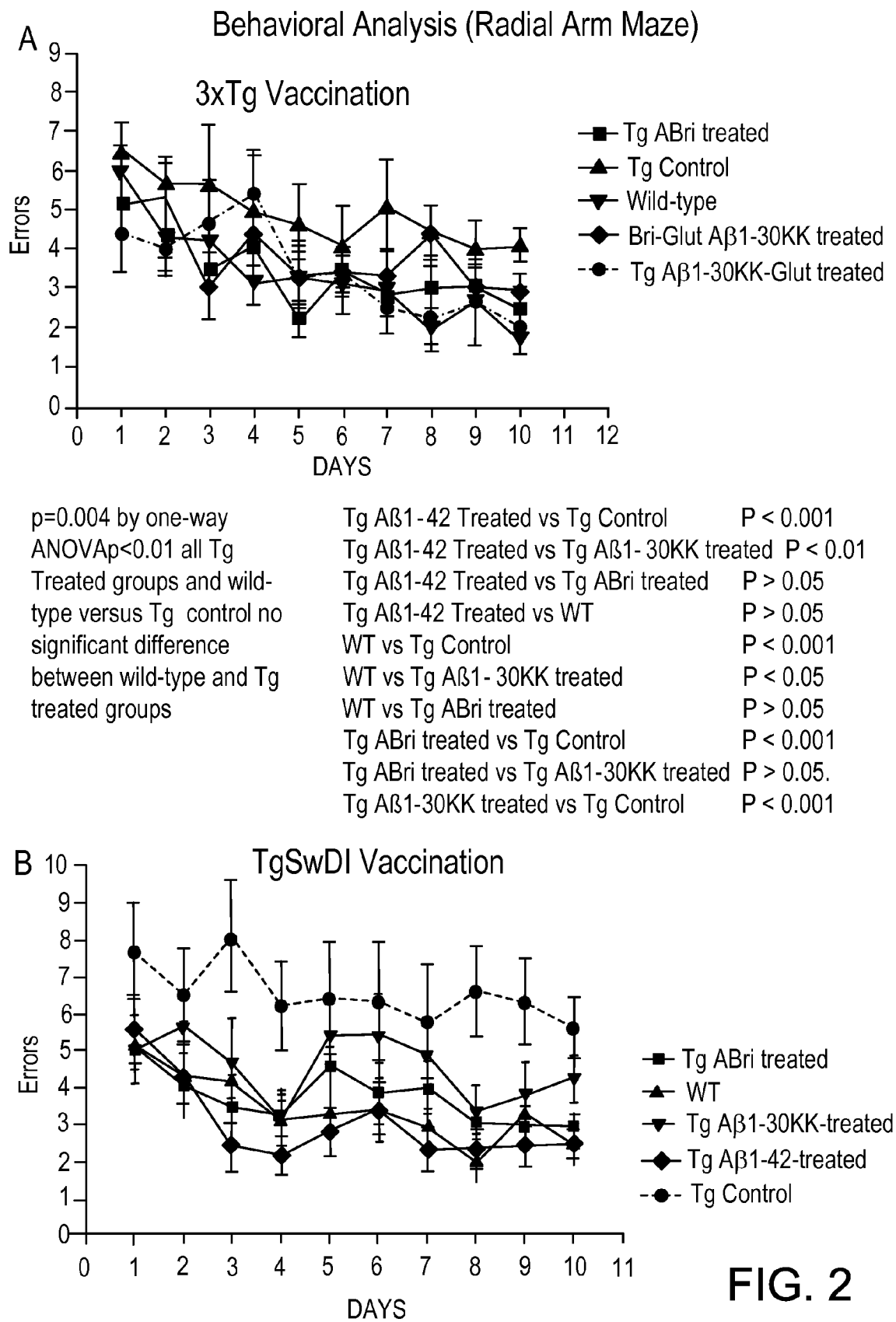
FIGS. 2A-2B are graphs showing the results of the Radial Arm Maze behavioral testing in 3×Tg (A) and TgSwDI (B) mice immunized with Aβ 1-30 $K_{18}K_{19}$ peptide (Aβ1-30KK) (SEQ ID NO: 1), vehicle control, polymerized British amyloidosis related peptides (pABri) (monomer sequence SEQ ID NO: 8), or a combination of Aβ 1-30KK and pABri.
Figure 3:
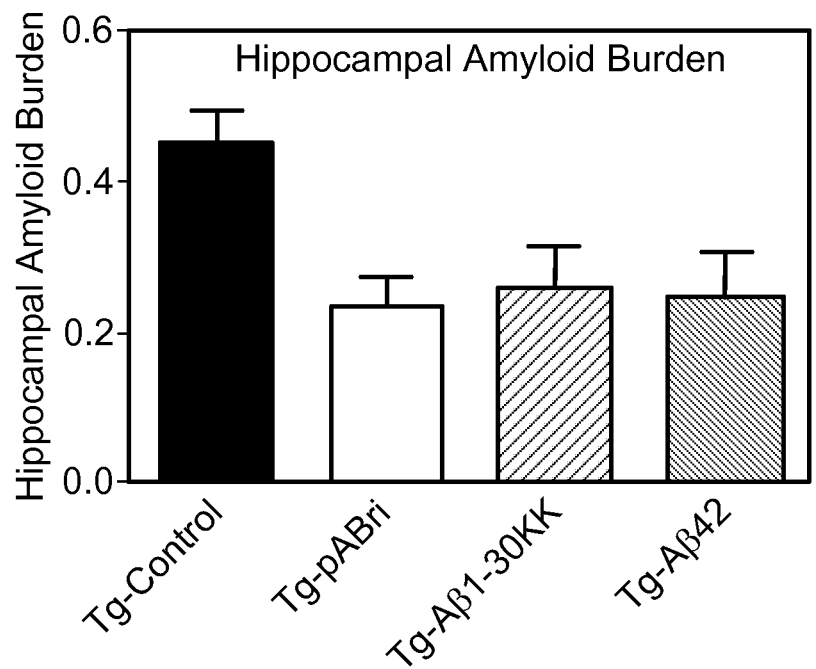
FIG. 3 is a graph showing immunohistological analysis of the hippocampal amyloid burden in TgSwDI mice immunized with Aβ 1-30 $K_{18}K_{19}$ peptide (Aβ1-30KK) (SEQ ID NO: 1), Aβ 1-42 peptide (SEQ ID NO: 9), vehicle control, or polymerized British amyloidosis related peptides (pABri) (monomer sequence SEQ ID NO: 8).

As shown in FIG. 1, a strong IgG immune response to all Aβ forms was observed when the test animals were immunized with modified Aβ peptide Aβ 1-30 $K_{18}K_{19}$. This effect was accompanied by a cognitive preservation (FIG. 2) and a significant reduction of cortical and hippocampal amyloid burden (FIG. 3) in both animal models.

Taken together, as demonstrated herein, immunization with modified Aβ peptide Aβ 1-30 $K_{18}K_{19}$ results in a statistically significant cognitive benefit and pathology burden reduction which makes this peptide an excellent candidate for immunotherapy of AD and other amyloid disorders.

EXAMPLE 2

3×Tg mice have both amyloid and Tau pathology (Oddo et al., Neurobiol. Aging, 24(8):1063-1070, 2003). This mouse model most closely resembles pathology in human Alzheimer's disease. Antibody PHF-1 detects Tau phosphorylated at Ser396/Ser404 (hyperphosphorylated Tau) (Bhaskar et al., Neuron, 68(1):19-31, 2010). PHF-1 immunoreactivity reflects Tau-related pathology.

FIGS. 4A-B show the PHF-1 immunohistochemical quantitation in the cortex (A) and CA1 hippocampus (B) of 3×Tg mice immunized with Aβ 1-30 $K_{18}K_{19}$ peptide (Aβ1-30KK)

(SEQ ID NO: 1), vehicle control, polymerized British amyloidosis related peptides (pABri) (monomer sequence SEQ ID NO: 8), or a combination of Aβ1-30KK and pABri. Tg-pABri and Tg combined treated mice show clear reductions in Tau pathology compared to controls, while Tg-Aβ1-30KK treated mice do not show Tau pathology reductions. FIG. 4C shows the amyloid burden in the hippocampus of control Tg, Tg pABri, TgAβ1-30KK and combination treated mice. All treated mice demonstrate a clear reduction in the amyloid burden compared to controls.

Figure 5:
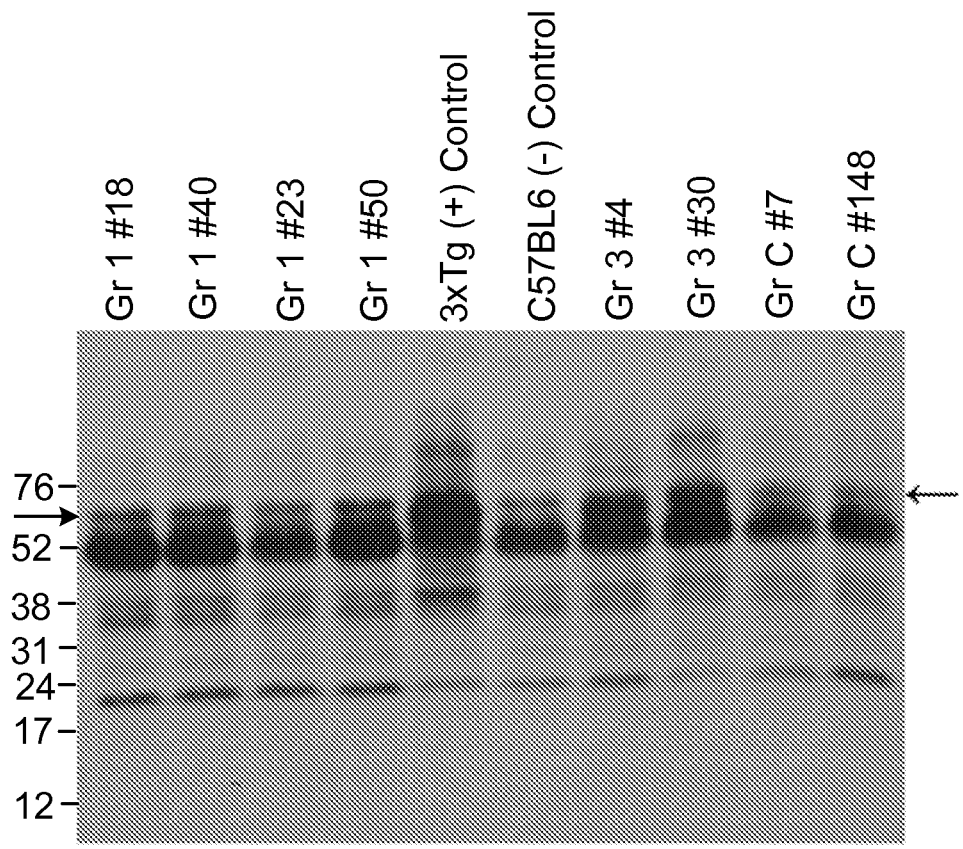
FIG. 5 shows an immunoblot developed with antibody PHF-1 which detects Tau phosphorylated at Ser396/Ser404 in soluble brain homogenates of 3×Tg mice immunized with Aβ 1-30 $K_{18}K_{19}$ peptide (Aβ1-30KK) (SEQ ID NO: 1), vehicle control, polymerized British amyloidosis related peptides (pABri) (monomer sequence SEQ ID NO: 8), or a combination of Aβ1-30KK and pABri. All treatment groups showed a marked reduction in the band at 65 kDa when compared to the Group 3 (controls inoculated with vehicle). The same result was repeated in all the animals of each group (n=8).

FIG. 5 shows an immunoblot developed with antibody PHF-1 in soluble brain homogenates. All treatments including Aβ 1-30 $K_{18}K_{19}$ peptide (Aβ1-30KK) (SEQ ID NO: 1) alone and the combination of Aβ1-30KK with pABri showed a marked reduction in the band at 65 kDa when compared to the Group 3 (controls inoculated with vehicle), with the most reduction seen in the combined treated group. The same result was repeated in all the animals of each group (n=8). The reduction in the band at 65 kDa reflects reductions in oligomers which are the toxic soluble form of phospho Tau (Yang et al., Journal of Alzheimer's Disease, 24(2):269-285, 2011; Scholtzova et al., Journal of Neuroscience, 29:1846-1854, 2009). The data show that although Aβ1-30KK has no sequence homology with Tau, it can influence the toxic oligomeric forms of Tau.

Comparison of FIGS. 4 and 5 confirms that Aβ1-30KK does not affect the precipitated tau but affects the soluble oligomeric form of pTau because it has a similar secondary structure to the one generated in the Aβ1-30KK.

Figure 6:
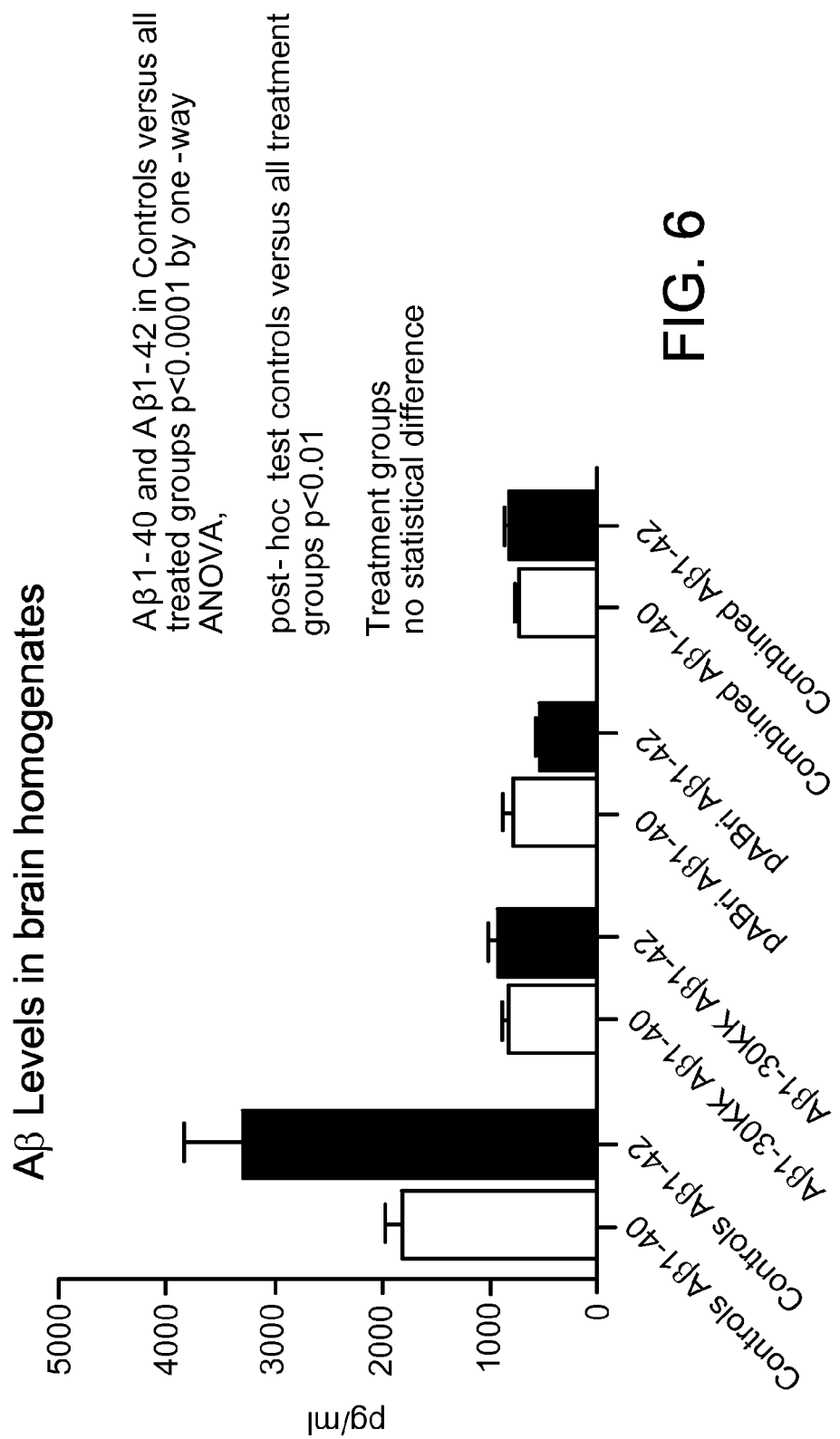
FIG. 6 is a bar graph showing the reduction, compared to controls, in soluble Aβ1-40 (SEQ ID NO: 10) and Aβ1-42 (SEQ ID NO: 9) in brain homogenates from 3×Tg mice treated with Aβ 1-30 $K_{18}K_{19}$ peptide (Aβ1-30KK) (SEQ ID NO: 1), pABri (monomer sequence SEQ ID NO: 8) or combined Aβ1-30KK with pABri.

FIG. 6 shows the reduction, compared to controls, in soluble Aβ1-40 (SEQ ID NO: 10) and Aβ1-42 (SEQ ID NO: 9) in brain homogenates from animals treated with Aβ 1-30 $K_{18}K_{19}$ peptide (Aβ31-30KK) (SEQ ID NO: 1), pABri (monomer sequence SEQ ID NO: 8) or combined Aβ1-30KK with pABri. In case of pABri, there is a proportional greater reduction in the soluble Aβ1-42 levels compared to soluble Aβ1-40 levels, demonstrating that the therapy acts more on the toxic oligomeric β-sheet structure of Aβ1-42 than on the less oligomeric Aβ1-40.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

Patents, patent applications, publications, product descriptions, and protocols are cited throughout this application, the disclosures of which are incorporated herein by reference in their entireties for all purposes.

The invention claimed is:

1. A polymerized form of an immunogenic modified Aβ peptide, which peptide contains Lysine substitutions in amino acid positions corresponding to amino acids 18 and 19 of Aβ 1-42, which polymerized form is soluble, non-fibrillogenic, has molecular weight less than 100 kDa, has the property of eliciting antibodies directed against the abnormal conformation of Aβ in amyloid plaques and/or in soluble and semi-soluble Aβ oligomers, and is produced using controlled polymerization of peptide monomers with glutaraldehyde.

2. The polymerized form of claim 1, wherein said modified Aβ peptide is selected from the group consisting of Aβ 1-30 $K_{18}K_{19}$ (DAEFRHDSGYEVHHQKLKKFAEDVGSNKGA; SEQ ID NO: 1), Aβ 1-40 $K_{18}K_{19}$ (DAEFRHDSGYEVHHQKLKKFAEDVGSNKGAIIGLMVGGVV; SEQ ID NO: 2), Aβ 1-42 $K_{18}K_{19}$ (DAEFRHDSGYEVHHQKLKKFAEDVGSNKGAIIGLMVGGVVIA; SEQ ID NO: 3), Aβ 1-20 $K_{18}K_{19}$ (DAEFRHDSGYEVHHQKLKKF; SEQ ID NO: 4), Aβ 10-30 $K_{18}K_{19}$ (YEVHHQKLKKFAEDVGSNKGA; SEQ ID NO: 5), Aβ 10-40 $K_{18}K_{19}$ (YEVHHQKLKKFAEDVGSNKGAIIGLMVGGVV; SEQ ID NO: 6), and Aβ 10-42 $K_{18}K_{19}$ (YEVHHQKLKKFAEDVGSNKGAIIGLMVGGVVIA; SEQ ID NO: 7).

3. A pharmaceutical composition comprising one or more of the polymerized forms of claim 1 and a pharmaceutically acceptable carrier or diluent.

4. The pharmaceutical composition of claim 3, further comprising an adjuvant.

* * * * *

UNITED STATES PATENT AND TRADEMARK OFFICE
CERTIFICATE OF CORRECTION

PATENT NO. : 8,906,382 B2
APPLICATION NO. : 13/553566
DATED : December 9, 2014
INVENTOR(S) : Thomas Wisniewski and Fernando R. Goni It is certified that error appears in the above-identified patent and that said Letters Patent is hereby corrected as shown below:

In the claims

Column 21, (line 50), Claim 1,
Line 8, "and/or in soluble and semi-soluble" should be "and/or insoluble and semi-soluble".

Signed and Sealed this
Fourteenth Day of June, 2016

Michelle K. Lee
*Director of the United States Patent and Trademark Office*

SEQUENCE LISTING

```
<160> NUMBER OF SEQ ID NOS: 10

<210> SEQ ID NO 1
<211> LENGTH: 30
<212> TYPE: PRT
<213> ORGANISM: Artificial Sequence
<220> FEATURE:
<223> OTHER INFORMATION: synthetic

<400> SEQUENCE: 1

Asp Ala Glu Phe Arg His Asp Ser Gly Tyr Glu Val His His Gln Lys
1               5                   10                  15

Leu Lys Lys Phe Ala Glu Asp Val Gly Ser Asn Lys Gly Ala
            20                  25                  30

<210> SEQ ID NO 2
<211> LENGTH: 40
<212> TYPE: PRT
<213> ORGANISM: Artificial Sequence
<220> FEATURE:
<223> OTHER INFORMATION: synthetic

<400> SEQUENCE: 2

Asp Ala Glu Phe Arg His Asp Ser Gly Tyr Glu Val His His Gln Lys
1               5                   10                  15

Leu Lys Lys Phe Ala Glu Asp Val Gly Ser Asn Lys Gly Ala Ile Ile
            20                  25                  30

Gly Leu Met Val Gly Gly Val Val
        35                  40

<210> SEQ ID NO 3
<211> LENGTH: 42
<212> TYPE: PRT
<213> ORGANISM: Artificial Sequence
<220> FEATURE:
<223> OTHER INFORMATION: synthetic

<400> SEQUENCE: 3
```

```
Asp Ala Glu Phe Arg His Asp Ser Gly Tyr Glu Val His His Gln Lys
1               5                   10                  15

Leu Lys Lys Phe Ala Glu Asp Val Gly Ser Asn Lys Gly Ala Ile Ile
                20                  25                  30

Gly Leu Met Val Gly Gly Val Val Ile Ala
            35                  40

<210> SEQ ID NO 4
<211> LENGTH: 20
<212> TYPE: PRT
<213> ORGANISM: Artificial Sequence
<220> FEATURE:
<223> OTHER INFORMATION: synthetic

<400> SEQUENCE: 4

Asp Ala Glu Phe Arg His Asp Ser Gly Tyr Glu Val His His Gln Lys
1               5                   10                  15

Leu Lys Lys Phe
            20

<210> SEQ ID NO 5
<211> LENGTH: 21
<212> TYPE: PRT
<213> ORGANISM: Artificial Sequence
<220> FEATURE:
<223> OTHER INFORMATION: synthetic

<400> SEQUENCE: 5

Tyr Glu Val His His Gln Lys Leu Lys Lys Phe Ala Glu Asp Val Gly
1               5                   10                  15

Ser Asn Lys Gly Ala
            20

<210> SEQ ID NO 6
<211> LENGTH: 31
<212> TYPE: PRT
<213> ORGANISM: Artificial Sequence
<220> FEATURE:
<223> OTHER INFORMATION: synthetic

<400> SEQUENCE: 6

Tyr Glu Val His His Gln Lys Leu Lys Lys Phe Ala Glu Asp Val Gly
1               5                   10                  15

Ser Asn Lys Gly Ala Ile Ile Gly Leu Met Val Gly Gly Val Val
            20                  25                  30

<210> SEQ ID NO 7
<211> LENGTH: 33
<212> TYPE: PRT
<213> ORGANISM: Artificial Sequence
<220> FEATURE:
<223> OTHER INFORMATION: synthetic

<400> SEQUENCE: 7

Tyr Glu Val His His Gln Lys Leu Lys Lys Phe Ala Glu Asp Val Gly
1               5                   10                  15

Ser Asn Lys Gly Ala Ile Ile Gly Leu Met Val Gly Gly Val Val Ile
            20                  25                  30

Ala

<210> SEQ ID NO 8
<211> LENGTH: 13
```

```
<212> TYPE: PRT
<213> ORGANISM: Artificial Sequence
<220> FEATURE:
<223> OTHER INFORMATION: synthetic

<400> SEQUENCE: 8

Cys Ser Arg Thr Val Lys Lys Asn Ile Ile Glu Glu Asn
 1               5                  10

<210> SEQ ID NO 9
<211> LENGTH: 42
<212> TYPE: PRT
<213> ORGANISM: Artificial Sequence
<220> FEATURE:
<223> OTHER INFORMATION: synthetic

<400> SEQUENCE: 9

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 10
<211> LENGTH: 40
<212> TYPE: PRT
<213> ORGANISM: Artificial Sequence
<220> FEATURE:
<223> OTHER INFORMATION: synthetic

<400> SEQUENCE: 10

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val
        35                  40
```